United States Patent
Strobel et al.

(10) Patent No.: US 7,338,956 B2
(45) Date of Patent: Mar. 4, 2008

(54) ACYLAMINO-SUBSTITUTED HETEROAROMATIC COMPOUNDS AND THEIR USE AS PHARMACEUTICALS

(75) Inventors: Hartmut Strobel, Liederbach (DE); Paulus Wohlfart, Bensheim (DE); Peter Below, Frankfurt (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 465 days.

(21) Appl. No.: 10/634,979

(22) Filed: Aug. 5, 2003

(65) Prior Publication Data

US 2004/0110808 A1 Jun. 10, 2004

Related U.S. Application Data

(60) Provisional application No. 60/432,314, filed on Dec. 10, 2002.

(30) Foreign Application Priority Data

Aug. 7, 2002 (EP) .................................. 02017585

(51) Int. Cl.
*C07D 417/12* (2006.01)
*A61K 31/428* (2006.01)

(52) U.S. Cl. ................. 514/255.05; 514/338; 514/361; 514/367; 546/270.1; 548/125; 548/163

(58) Field of Classification Search ............ 546/270.1; 548/125, 163; 514/255.05, 338, 361, 367
See application file for complete search history.

(56) References Cited

U.S. PATENT DOCUMENTS

| | | | | |
|---|---|---|---|---|
| 2,399,026 | A * | 4/1946 | Henzi | 548/163 |
| 4,560,549 | A * | 12/1985 | Ritchey | 424/431 |
| 4,675,331 | A * | 6/1987 | Kume et al. | 514/367 |
| 4,929,623 | A * | 5/1990 | Abe et al. | 514/293 |
| 6,020,470 | A * | 2/2000 | Ueno et al. | 534/635 |
| 6,342,514 | B1 * | 1/2002 | Petrie et al. | 514/367 |
| 6,521,754 | B2 * | 2/2003 | Alanine et al. | 544/129 |
| 6,617,359 | B2 | 9/2003 | Strobel et al. | |
| 6,759,412 | B2 | 7/2004 | Strobel | |
| 6,812,253 | B2 | 11/2004 | Strobel et al. | |
| 6,949,556 | B2 | 9/2005 | Strobel | |
| 2003/0055093 | A1 | 3/2003 | Strobel | |
| 2003/0134859 | A1 | 7/2003 | Yoshiya et al. | |
| 2004/0082628 | A1 | 4/2004 | Strobel | |
| 2004/0092513 | A1 | 5/2004 | Strobel | |
| 2004/0225013 | A1 | 11/2004 | Strobel | |
| 2005/0054729 | A1 | 3/2005 | Strobel | |
| 2005/0101599 | A1 | 5/2005 | Zeiher | |

FOREIGN PATENT DOCUMENTS

| | | | |
|---|---|---|---|
| EP | 1 277 729 A1 | | 1/2003 |
| FR | 2121394 | | 8/1972 |
| GB | 1345552 | * | 1/1974 |
| GB | 1596383 | * | 8/1981 |
| WO | WO 98/11073 | | 3/1998 |
| WO | WO 99/47153 | | 9/1999 |
| WO | WO 00/03746 | | 1/2000 |
| WO | WO 00/27394 | | 5/2000 |
| WO | WO 00/27819 | | 5/2000 |
| WO | WO 01/97786 | | 12/2001 |
| WO | WO 02/34711 A1 | | 5/2002 |
| WO | WO 02/064146 A1 | | 8/2002 |
| WO | WO 02/064545 A1 | | 8/2002 |
| WO | WO 02/064546 A2 | | 8/2002 |
| WO | WO 02/064565 A1 | | 8/2002 |

OTHER PUBLICATIONS

Bellasio E et al., Sostanze A Potenziale Azione Cardiovascolare. 2-acilaminobenzimidazoli ad attivita ipotensiva, Farmaco, Ed. Sc., vol. 28, 2, 1978, pp. 164-182.

Bogoslowskii et al, Synthesis of some Derivatives of Aminoquinolines, Zhurnal Obshchei Khimii; vol. 14; 1944; pp. 316-318.

Buscemi et al, Heterocyclic Photorearrangements. Photochemical Behaviour of Some 3,5-Disubstituted 1,2,4-Oxadiazoles in Methanol at 254 nm., Journal of Heterocyclic Chem.; vol. 25; May-Jun. 1988; pp. 931-935.

(Continued)

*Primary Examiner*—Fiona T Powers
(74) *Attorney, Agent, or Firm*—Jiang Lin

(57) ABSTRACT

The present invention relates to acylamino-substituted heteroaromatic compounds of formula I,

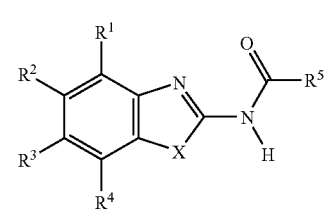

wherein $R^1$, $R^2$, $R^3$, $R^4$ and $R^5$ and X are as defined herein, to pharmaceutical compositions comprising such compounds, to methods for the stimulation of the expression of endothelial NO synthase, and methods of treatment comprising administering such compounds.

6 Claims, No Drawings

OTHER PUBLICATIONS

Buscemi et al., Heterocyclic Photorearrangements. Photoinduced Rearrangements of 1,2,4-Oxadiazoles Substituted by an XYZ Side Chain Sequence, Journal of Heterocyclic Chem.; vol. 25; Sep.-Oct. 1988; pp. 1551-1553.

Elina et al, Tautomerism of 2-Acetylaminoquinoxalines and Their N-Oxides, Chem. Heterocyclic Compd.(Eng. transl.); No. 2; 1996; pp. 72-76.

Endres M et al., Stroke protection by 3-hydroxy-3-methylglutaryl (HMG)-CoA reductase inhibitors mediated by endothelial nitric oxide synthase, Proc. Natl. Aca. Sci. USA 95, 1998, vol. 95, pp. 8880-8885.

Harsanyi et al, Redox-Aromatisierung des 2-Oximino-1.2.3.4-tetrahydrochinoxalins und seiner Acylderivate, Chem. Ber.; No. 105; 1972; pp. 813-819.

Khristich et al, The Benzoylation of 2-Amino-1-Methylbenzimidazole, Chem. Heterocycl. Compd. (Eng. Transl.); No. 9; 1973; p. 1174.

Khristich, B.I., et al., Synthesis and Transformations of 2-Amino-3-Acyl-1-Methylbenzimidazolium Salts, Chemistry of Heterocyclic Compounds (Eng. Translation), No. 10, Oct. 1974, pp. 1225-1228.

Laufs Ulrich et al., Upregulation of Endothelial Nitric Oxide Synthase by HMG CoA Reductase Inhibitors, Circulation 97, 1998, pp. 1129-1135.

Li Huige et al., Activation of Protein Kinase C(alpha) and/or (epsilon) Enhances Transciption of the Human Endothelial Nitric Oxide Synthase Gene, Mol. Pharmacol., 1998, vol. 53, pp. 630-637.

Moroi Masao et al., Interaction of Genetic Deficiency of Endothelial Nitric Oxide, Gender, and Pregnancy in Vascular Response to Injury in Mice, J. Clin. Invest., 1998, vol. 101, No. 6, pp. 1225-1232.

Nakayama Masafumi et al., T-786—>C Mutation in the 5'-Flanking Region of the Endothelial Nitric Oxide Synthase Gene Is Associated with Coronary Spasm, Clinical Investigation and Reports, Circulation 99, 1999, pp. 2864-2870.

Pilyugin V.S., et al., Synthesis and Biological Activity of Derivatives of 2-Aminobenzimidazole and Carboxylic Acids (Eng. translation), Bashk. Khim. Zh. 2001, Tom 8, No. 1, pp. 18-25.

Popov et al, Condensation of 2-Aminobenzimidazoles with o-Substituted Benzoyl Chlorides, Chem. Heterocyclic Comp. (Eng. Transl.); vol. 25(2); 1989; p. 229.

Rao et al, Synthesis of 2-Aryl-1H-s-Triazolo[1,5-a]Benzimidazoles, Synthetic Communications; No. 18; 1988; pp. 1995-2001.

Sessa William C et al., Chronic Exercise in Dogs Increases Coronary Vascular Nitric Oxide Production and Endothelial Cell Nitric Oxide Synthase Gene Expression, Circulation Research, 1994, vol. 74, No. 2, pp. 349-353.

Shepard et al, Carboxylic N,N-Diphenylcarbamic Anhydrides, New Acylating Agents, Journal Heterocyclic Chem.; No. 16; 1979; pp. 321-325.

Shiokawa et al, Studies on Benzimidazoles and related Compounds. IV. Reactivity of 2-Azido-1-methylbenzimidazole, Chem. Pharm. Bulletin; No. 19; 1971; pp. 401-408.

Simonov M., et al., Derivatives of 2-Amino-1-Methylbenzimidazole-5-Carboxylic Acid, Journal of General Chemistry of the USSR (Eng. translation), V32, 1962, pp. 2194-2196.

Takahashi et al, 1,3-Dipolar Cycloaddition Reaction with 1-Methylbenzimidazole 3-Oxide,Tetrahedron Letters No. 25; 1963; pp. 1687-1691.

Takahashi et al, Benzimiidazole N-Oxides. IV. 1,3-Dipolar Cycloaddition Reaction with 1-Methylbenzimidazole 3-Oxide, Chem, Pharm. Bull.; vol. 12; 1964; pp. 1290-1295.

Tamura et al, Syntheses and Properties of 3-Acylimino-1-alkylimidazolium and Benzimidazolium Betaines, Journal Heterocyclic Chem.; vol. 11; 1974; pp. 781-785.

Van Allen et al, The Reaction of Certain Heterocyclic Azides and triphenylphosphine, Journal Heterocyclic Chem; No. 5; Aug. 1968; pp. 471-476.

Varenne Olivier et al., Percutaneous Gene Thereapy Using Recombinant Adenoviruses Encoding Human Herpes Simplex Virus Thymidine Kinase, Human PAI-1, and Human NOS3 in Balloon-Injured Procine Coronary Arteries, Human Gene Thereapy,2000, vol. 11, pp. 1329-1339.

Wolf et al, Substituted Sulfaquinoxalines. Extension of the Glyoxalate Synthesis of 2-Aminoquinoxaline, J. Amer. Chem. Soc.; vol. 71; 1949; pp. 6-8.

Wolf et al, Substituted Sulfaquinoxalines. Some Derivatives and Isomers of 2-Sulfanilamidoquinoxaline, J. Amer. Chem. Soc.; vol. 70; 1948; p. 2572.

Bourdais, Jacques, 2-Mathylindole-3-carboxylic acid amide derivatives, Chemical Abstract summary CA78:136065 (1972).

* cited by examiner

ACYLAMINO-SUBSTITUTED HETEROAROMATIC COMPOUNDS AND THEIR USE AS PHARMACEUTICALS

This application claims the benefit of U.S. Provisional Application No. 60/432,314, filed Dec. 10, 2002. The content of U.S. Provisional Application No. 60/432,314 is incorporated herein by reference.

FIELD OF THE INVENTION

The present invention relates to acylamino-substituted heteroaromatic compounds of the formula I,

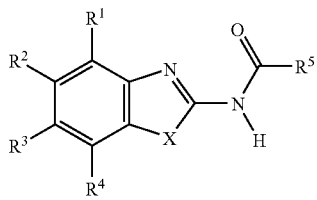

wherein $R^1$, $R^2$, $R^3$, $R^4$ and $R^5$ and X have the meanings indicated below. The compounds of formula I are valuable pharmaceutically active compounds which are useful in the treatment of various disease states including cardiovascular disorders such as atherosclerosis, thrombosis, coronary artery disease, hypertension and cardiac insufficiency. They upregulate the expression of the enzyme endothelial nitric oxide (NO) synthase and can be applied in conditions in which an increased expression of said enzyme or an increased NO level or the normalization of a decreased NO level is desired. The invention furthermore relates to processes for the preparation of compounds of the formula I, their use, in particular as active ingredients in pharmaceuticals, and pharmaceutical preparations comprising them.

BACKGROUND OF THE INVENTION

Endothelial NO synthase (eNOS, NOS-III) belongs to a group of three isoenzymes which produce nitric oxide (NO) by oxidation of arginine. Endothelially released NO is of central importance in a number of key cardiovascular mechanisms. It has a vasodilating effect and inhibits the aggregation of platelets, the adhesion of leukocytes to the endothelium and the proliferation of intimal smooth muscle cells.

Endothelial NO synthase is subject to physiological and pathophysiological regulation both at the transcriptional and at the post-transcriptional level. Enzyme already present in the endothelium may undergo calcium-dependent and calcium-independent activation through phosphorylation of specific amino acids, but also by direct interactions with specific proteins. Stimulators of this, usually transient, NO release are, extracellular arginine, 17β-estrogen and the mechanical stimulus exerted on the luminal surface of the endothelium by the blood flow (shear stress). The latter additionally leads to regulation of eNOS at the transcriptional level. Thus, for example, Sessa et al. (Circ. Research 74 (1994) 349, the content of which is incorporated herein by reference) were able by means of exercise training and the increase in shear stress associated therewith to obtain a marked increase in eNOS.

Whether regulation at the post-transcriptional level is relevant in vivo, has not been unambiguously proven. Thus, for example, administration of a high arginine dose is followed by only a transient improvement in the endothelium-dependent vasorelaxation in patients with coronary heart disease.

On the other hand, the significance of the upregulation of the eNOS protein is scientifically accepted. Thus, there are findings which show that the protective properties of the HMG-CoA reductase inhibitor simvastatin can be attributed, besides to the lipid lowering effect, also in part to an increase in eNOS expression in vivo (Endres et al., Proc. Natl. Acad. Sci. USA 95 (1998) 8880, the content of which is incorporated herein by reference). It is additionally known that single point mutations in the 5'-flanking region of the eNOS gene ("eNOS promoter"), and the reduction in the rate of eNOS gene transcription associated therewith, in the Japanese population is associated with an increase in the risk of coronary spasms (Nakayama et al., Circulation 99 (1999) 2864, the content of which is incorporated herein by reference).

The current assumption therefore is that the transcriptional and post-transcriptional mechanisms of eNOS regulation are seriously disturbed in a large number of disorders, especially in cardiovascular disorders. Even in very early stages of a wide variety of cardiovascular disorders it is possible for a dysfunction of this type in the endothelium lining the blood vessels to lead to a deficiency of bioactive NO, which is manifested as the disorder progresses in the form of measurable pathophysiological and morphological changes. Thus, critical steps in early atherogenesis are speeded up by a decrease in endothelial NO release, such as, for example, the oxidation of low density lipoproteins, the recruitment and deposition of monocytes in the intima of vessels, and the proliferation of intimal cells. A consequence of atherogenesis is the formation of plaques on the inside of the blood vessels, which may in turn lead, through a diminution in the shear stress, to a further decrease in endothelial NO release and a further deterioration in the pathology. Since endothelial NO is also a vasodilator, a decrease thereof frequently also leads to hypertension, which may, as an independent risk factor, cause further organ damage.

The aim of a therapeutic approach to the treatment of these disorders must accordingly be to interrupt this chain of events by increasing the endothelial NO expression. Gene transfer experiments which lead in vitro to overexpression of NO synthase in previously damaged vessels are in fact able to counteract the described processes and are thus evidence of the correctness of this approach (Varenne et al., Hum. Gene Ther. 11 (2000) 1329, the content of which is incorporated herein by reference).

Some low molecular weight compounds that, in cell cultures, may lead to a direct effect on eNOS transcription and expression are disclosed in the literature. The statins which have already been mentioned are, however, the only substances for which it has been possible to date to show such an increase in eNOS in vivo as a side effect. But in view of the known range of side effects of this class of substances it is unclear how far this effect is present in a toxicologically unproblematic dose.

Liao et al. claim in WO 99/47153 and WO 00/03746 (the content of which is incorporated herein by reference) the use of rhoGTPase inhibitors and agents which influence the organization of the actin cytoskeleton for increasing eNOS in endothelial cells and for the therapy of various disorders such as, for example, stroke or pulmonary hypertension without, however, indicating a specific way of achieving this.

WO 02/064146, WO 02/064545, WO 02/064565 and WO 02/064546 (the content of which is incorporated herein by reference) disclose acylated, benzo-condensed cycloalkenylamines which upregulate eNOS expression in endothelial cells and are useful pharmaceutically active ingredients for the treatment of various diseases, but there is an ongoing need for further eNOS expression enhancers with a favorable: property profile. The present invention satisfies this need by providing compounds of the formula I and methods of using them.

Certain acylamino-substituted heteroaromatic compounds of the formula I have already been described. In many cases the known compounds have been prepared in the course of merely chemical investigations or for use as intermediates in the synthesis of other compounds, and no biological activity of them has been described. Compounds of the formula I and structurally similar compounds for which a pharmaceutical activity has already been described include, for example, certain hypotensive 2-acetylaminobenzimidazoles (Bellasio et al., Farmaco, Ed. Sci., 28 (1973) 164, the content of which is incorporated herein by reference) which, however, do not suggest the 2-(hetero)aroylaminobenzimidazoles comprised by the present invention and their biological activity. The activating effect on guanylate cyclase of certain N-benzimidazolylcarboxamides and N-benzothiazolylcarboxamides described in WO 00/27394 (the content of which is incorporated herein by reference) seems to depend on the presence of a 3-(3-(dimethylamino)propoxy)-1-(phenylmethyl)-1H-pyrazol-5-carboxamide moiety. In WO 01/97786 (the content of which is incorporated herein by reference) the adenosine receptor affinity of certain N-benzothiazolylcarboxamides has been disclosed. In WO 01/83427, WO 98/11073 and Pilyugin et al., Bashkirskii Khimicheskii Zhurnal 8 (2001) 18 (the content of which is incorporated herein by reference), it has been described that similar compounds exhibit a hypoglycemic activity, antiviral activity or antifungal activity, respectively. There are no indications in the prior art that compounds of the formula I would upregulate the expression of endothelial NO synthase, but it is surprising that they exhibit this activity and therefore are valuable pharmaceutically active ingredients which are useful in the treatment of a variety of diseases including cardiovascular diseases such as, for example, atherosclerosis, thrombosis, coronary artery disease, hypertension and cardiac insufficiency.

SUMMARY OF THE INVENTION

A subject of the present invention are novel acylamino-substituted heteroaromatic compounds of the formula I,

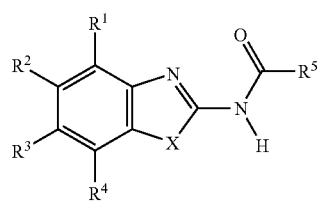

I in any of their stereoisomeric forms and mixtures thereof in any ratio, and the pharmaceutically acceptable salts thereof, wherein in the formula I:

$R^1$ and $R^4$ are each independently selected from the group consisting of: H; unsubstituted and at least monosubstituted $C_1$-$C_{10}$-alkyl, $C_2$-$C_{10}$-alkenyl and $C_2$-$C_{10}$-alkynyl, the substituents of which are selected from the group consisting of F, OH, $C_1$-$C_8$-alkoxy, $C_1$-$C_8$-alkylmercapto, —CN, $COOR^6$, $CONR^7R^8$, and unsubstituted and at least monosubstituted phenyl and heteroaryl where the substituents of the phenyl and heteroaryl groups are selected from the group consisting of halogen, —CN, $C_1$-$C_3$-alkyl, $C_1$-$C_3$-alkoxy and $CF_3$; unsubstituted and at least monosubstituted phenyl and heteroaryl the substituents of which are selected from the group consisting of halogen, —CN, $C_1$-$C_3$-alkyl, $C_1$-$C_3$-alkoxy and $CF_3$; $COR^9$; $CONR^{10}R^{11}$; $COOR^{12}$; $CF_3$; halogen; —CN; $NR^{13}R^{14}$; $OR^{15}$; $S(O)_m R^{16}$; $SO_2NR^{17}R^{18}$; and $NO_2$;

$R^2$ and $R^3$ are independently from each other selected from the group consisting of: H; halogen; —CN; unsubstituted and at least monosubstituted $C_1$-$C_{10}$-alkyl the substituents of which are selected from the group consisting of OH, phenyl, and heteroaryl; OH; $C_1$-$C_{10}$-alkoxy; phenoxy; $S(O)_m R^{19}$; $CF_3$; $NO_2$; $C_1$-$C_{10}$-alkylamino; di($C_1$-$C_{10}$-alkyl)amino; ($C_1$-$C_6$-alkyl)-CONH—; unsubstituted and at least monosubstituted phenyl-CONH— and phenyl-$SO_2$—O— the substituents of which are selected from the group consisting of halogen, —CN, methyl and methoxy; $C_1$-$C_6$-alkyl-$SO_2$—O—; unsubstituted and at least monosubstituted ($C_1$-$C_6$-alkyl)-CO— the substituents of which are selected from the group consisting of F, di($C_1$-$C_3$-alkyl)amino, pyrrolidinyl and piperidinyl; and phenyl-CO— the phenyl part of which is unsubstituted or at least monosubstituted by substituents selected from the group consisting of $C_1$-$C_3$-alkyl, halogen and methoxy;

$R^5$ is a group Ar or a group Hetar both of which are unsubstituted or carry one or more identical or different substituents selected from the group consisting of: halogen; —CN; $NH_2$; unsubstituted and at least monosubstituted $C_1$-$C_{10}$-alkyl, $C_2$-$C_{10}$-alkenyl, $C_2$-$C_{10}$-alkynyl, $C_1$-$C_{10}$-alkoxy, $C_1$-$C_{10}$-alkylamino and di($C_1$-$C_{10}$-alkyl)amino, the substituents of which are selected from the group consisting of F, OH, $C_1$-$C_8$-alkoxy, aryloxy, $C_1$-$C_8$-alkylmercapto, $NH_2$, $C_1$-$C_8$-alkylamino and di($C_1$-$C_8$-alkyl)amino; $C_3$-$C_5$-alkandiyl; phenyl; heteroaryl; aryl-substituted or heteroaryl-substituted $C_1$-$C_4$-alkyl; $CF_3$; $NO_2$; OH; phenoxy; benzyloxy; ($C_1$-$C_{10}$-alkyl)-COO—; $S(O)_m R^{20}$; SH; phenylamino; benzylamino; ($C_1$-$C_{10}$-alkyl)-CONH—; ($C_1$-$C_{10}$-alkyl)-CO—N($C_1$-$C_4$-alkyl)-; phenyl-CONH—; phenyl-CO—N($C_1$-$C_4$-alkyl)-; heteroaryl-CONH—; heteroaryl-CO—N($C_1$-$C_4$-alkyl)-; ($C_1$-$C_{10}$-alkyl)-CO—; phenyl-CO—; heteroaryl-CO—; $CF_3$—CO—; —$OCH_2O$—; —$OCF_2O$—; —$OCH_2CH_2O$—; —$CH_2CH_2O$—; $COOR^{21}$; $CONR^{22}R^{23}$; $C(NH)$—$NH_2$; $SO_2NR^{24}R^{25}$; $R^{26}SO_2NH$—; $R^{27}SO_2N(C_1$-$C_6$-alkyl)-; and a residue of a saturated or at least monounsaturated aliphatic, monocyclic 5-membered to 7-membered heterocycle containing 1, 2 or 3 heteroatoms selected from the group consisting of N, O and S, which heterocycle can be substituted by one or more substituents selected from the group consisting of halogen, $C_1$-$C_3$-alkyl, $C_1$-$C_3$-alkoxy, OH, oxo and $CF_3$, where said heterocycle can optionally be condensed to the said group Ar or the said group Hetar; wherein all aryl, heteroaryl, phenyl, aryl-containing, heteroaryl-containing and phenyl-containing groups, which are optionally present in the said substituents of the said group Ar or the said group Hetar, can be substituted by one or more substituents selected from the group consisting of halogen, —CN, $C_1$-$C_3$-alkyl, OH, $C_1$-$C_3$-alkoxy, and $CF_3$;

$R^6$ is selected from the group consisting of:

H; $C_1$-$C_{10}$-alkyl which can be substituted by one or more substituents selected from the group consisting of F, $C_1$-$C_8$-alkoxy and di($C_1$-$C_8$-alkyl)amino; aryl-($C_1$-$C_4$-alkyl)- and heteroaryl-($C_1$-$C_4$-alkyl)-both of which can be substituted by one or more substituents selected from the group consisting of halogen, $C_1$-$C_4$-alkyl, $C_1$-$C_4$-alkoxy and di($C_1$-$C_6$-alkyl)amino;

$R^7$ is selected from the group consisting of:

H; $C_1$-$C_{10}$-alkyl which can be substituted by one or more substituents selected from the group consisting of F, $C_1$-$C_8$-alkoxy, di($C_1$-$C_8$-alkyl)amino and phenyl; phenyl; indanyl; and heteroaryl; wherein each of the aromatic groups can be unsubstituted or carry one or more substituents selected from the group consisting of halogen, —CN, $C_1$-$C_3$-alkyl, $C_1$-$C_3$-alkoxy and $CF_3$;

$R^8$ is H or $C_1$-$C_{10}$-alkyl;

$R^9$ is selected from the group consisting of:

$C_1$-$C_{10}$-alkyl which can be substituted by one or more substituents from the group consisting of F, $C_1$-$C_4$-alkoxy and di($C_1$-$C_3$-alkyl)amino; and unsubstituted and at least monosubstituted phenyl and heteroaryl the substituents of which are selected from the group consisting of $C_1$-$C_3$-alkyl, $C_1$-$C_3$-alkoxy, halogen, —CN and $CF_3$;

$R^1$, independently from $R^7$, is defined as $R^7$;

$R^{11}$, independently from $R^8$, is defined as $R^8$;

$R^{12}$, independently from $R^6$, is defined as $R^6$;

$R^{13}$ is selected from the group consisting of:

H; $C_1$-$C_6$-alkyl; unsubstituted and substituted phenyl, benzyl, heteroaryl, ($C_1$-$C_6$-alkyl)-CO—, phenyl-CO—, and heteroaryl-CO—, the substituents of which are selected from the group consisting of halogen, —CN, $C_1$-$C_3$-alkyl, $C_1$-$C_3$-alkoxy and $CF_3$, wherein one or more of these substituents can be present;

$R^{14}$, independently from $R^{13}$, is defined as $R^{13}$;

$R^{15}$ is selected from the group consisting of:

H; $C_1$-$C_{10}$-alkyl; ($C_1$-$C_3$-alkoxy)-$C_1$-$C_3$-alkyl- and substituted and unsubstituted benzyl, phenyl and heteroaryl, the substituents of which are selected from the group consisting of halogen, —CN, $C_1$-$C_3$-alkyl, $C_1$-$C_3$-alkoxy and $CF_3$, wherein one or more of these substituents can be present;

$R^{16}$ is selected from the group consisting of:

$C_1$-$C_{10}$-alkyl which can be substituted by one or more substituents selected from the group consisting of F, OH, $C_1$-$C_8$-alkoxy, aryloxy, $C_1$-$C_8$-alkylmercapto, $C_1$-$C_8$-alkylamino and di($C_1$-$C_8$-alkyl)amino; $CF_3$; and substituted and unsubstituted phenyl and heteroaryl, the substituents of which are selected from the group consisting of halogen, —CN, $C_1$-$C_3$-alkyl, $C_1$-$C_3$-alkoxy and $CF_3$, wherein one or more of these substitutents can be present;

$R^{17}$, independently from $R^7$, is defined as $R^7$;

$R^{18}$, independently from $R^8$, is defined as $R^8$;

$R^{19}$, independently from $R^{16}$, is defined as $R^{16}$;

$R^{20}$, independently from $R^{16}$, is defined as $R^{16}$;

$R^{21}$, independently from $R^6$, is defined as $R^6$;

$R^{22}$, independently from $R^7$, is defined as $R^7$;

$R^{23}$, independently from $R^8$, is defined as $R^8$;

$R^{24}$, independently from $R^7$, is defined as $R^7$;

$R^{25}$, independently from $R^8$, is defined as $R^8$;

$R^{26}$, independently from $R^{16}$, is defined as $R^{16}$;

$R^{27}$, independently from $R^{16}$, is defined as $R^{16}$;

$R^{30}$ is selected from the group consisting of: H; unsubstituted and at least monosubstituted $C_1$-$C_{10}$-alkyl, $C_2$-$C_{10}$-alkenyl and $C_2$-$C_{10}$-alkynyl, the substituents of which are selected from the group consisting of F, OH, $C_1$-$C_8$-alkoxy, $C_1$-$C_8$-alkylmercapto, —CN, $COOR^{31}$, $CONR^{32}R^{33}$, $NR^{34}R^{35}$, ($C_1$-$C_8$-alkyl)-CONH—, ($C_1$-$C_8$-alkoxy)-CONH—, benzyloxy-CONH— and unsubstituted and at least monosubstituted phenyl and heteroaryl where the substituents of the phenyl and heteroaryl groups are selected from the group consisting of halogen, —CN, $C_1$-$C_3$-alkyl, $C_1$-$C_3$-alkoxy and $CF_3$; and unsubstituted and at least monosubstituted phenyl and heteroaryl the substituents of which are selected from the group consisting of halogen, —CN, $C_1$-$C_3$-alkyl, $C_1$-$C_3$-alkoxy and $CF_3$;

$R^{31}$, independently from $R^6$, is defined as $R^6$;

$R^{32}$, independently from $R^6$, is defined as $R^6$;

$R^{33}$, independently from $R^6$, is defined as $R^6$;

$R^{34}$, independently from $R^6$, is defined as $R^6$;

$R^{35}$, independently from $R^6$, is defined as $R^6$;

X is selected from the group consisting of $NR^{30}$, S, O, CH=CH, N=CH and CH=N;

heteroaryl is a residue of a 5-membered to 10-membered, aromatic, monocyclic or bicyclic heterocycle containing one or more heteroatoms selected from the group consisting of N, O and S;

the group Hetar is a residue of a 5-membered to 10-membered, aromatic, monocyclic or bicyclic heterocycle containing one or more heteroatoms selected from the group consisting of N, O and S;

aryl is phenyl, naphth-1-yl or naphth-2-yl;

the group Ar is phenyl, naphth-1-yl or naphth-2-yl; and m is 0, 1 or 2.

DETAILED DESCRIPTION OF THE INVENTION

Definition of Terms

As used above, and throughout the description of the invention, the following terms, unless otherwise indicated, shall be understood to have the following meanings.

If groups or substituents in the compounds of the formula I such as, for example, aryl, heteroaryl, alkyl etc., can be present several times, they all independently from each other have the meanings indicated and can hence, in each individual case, be identical with or different from each other. As an example the di($C_1$-$C_{10}$-alkyl)amino group may be mentioned in which the alkyl substituents can be identical or different. When a group in the compounds of the formula I can be at least monosubstituted, or when it carries one or more substituents, it can be substituted, for example, by one, two, three, four or five substituents. When a group is substituted by two or more substituents, the substituents can be identical or different from each other.

When a substituent group is defined in terms of another substituent group, and these are indicated to be independent of each other, for example, as in the phrases, "$R^{10}$, independently from $R^7$, is $R^7$", or "$R^{10}$, independently from $R^7$, is defined as $R^7$", this means that they take on the same nature and range of values, but that they individually may be the same or different.

Alkyl, alkenyl and alkynyl residues can be linear or branched, acyclic or cyclic. This also applies when they are part of other groups, for example alkoxy groups, alkoxycarbonyl groups or substituted amino groups, or when they are substituted.

Examples of alkyl groups are methyl, ethyl, propyl, butyl, pentyl, hexyl, heptyl, octyl, nonyl, decyl, the n-isomers of these residues, isopropyl, isobutyl, isopentyl, sec-butyl, tert-butyl, neopentyl, 3,3-dimethylbutyl. The term alkyl here also expressly includes cycloalkyl groups and cycloalkyl-alkyl-groups (i.e., alkyl substituted by cycloalkyl) which groups contain at least three carbon atoms. Examples of such cycloalkyl residues are cyclopropyl, cyclobutyl, cyclopentyl, cyclohexyl, cycloheptyl and cyclooctyl. All cycloalkyl groups can be substituted by one or more identical or different $C_1$-$C_4$-alkyl residues, in particular by methyl. Examples of substituted cycloalkyl residues are 4-methylcyclohexyl, 4-tert-butylcyclohexyl or 2,3-dimethylcyclopentyl. Furthermore, unless stated otherwise, the term alkyl here also includes unsubstituted alkyl residues as well as alkyl residues which are substituted by one or more, for example 1, 2, 3 or 4, identical or different residues, for example aryl groups. In substituted alkyl residues, for example arylalkyl-, hydroxyalkyl-such as hydroxy-($C_1$-$C_3$)-alkyl- or alkoxyalkyl-such as $C_1$-$C_4$-alkyl-O—($C_1$-$C_3$)-alkyl-, the substituents can be present in any desired position.

Examples of alkenyl and alkynyl groups are vinyl, 1-propenyl, 2-propenyl (i.e. allyl), 2-butenyl, 2-methyl-2-propenyl, 3-methyl-2-butenyl, ethynyl, 2-propynyl (i.e. propargyl), 2-butynyl or 3-butynyl. The term alkenyl here also expressly includes cycloalkenyl groups and cycloalkenyl-alkyl-groups (i.e. alkyl substituted by cycloalkenyl) which groups contain at least three carbon atoms. Examples of cycloalkenyl residues are cyclopentenyl, cyclohexenyl, cycloheptenyl and cyclooctenyl. All cycloalkenyl groups can be substituted by one or more identical or different $C_1$-$C_4$-alkyl residues, in particular by methyl. Furthermore, unless stated otherwise, the term alkenyl and alkynyl here also includes unsubstituted alkenyl and alkynyl residues as well as alkenyl and alkynyl residues which are substituted by one or more, for example 1, 2, 3 or 4, identical or different residues, for example aryl groups. In substituted alkenyl and alkynyl residues, for example arylalkenyl-, hydroxyalkenyl-such as hydroxy-($C_2$-$C_3$)-alkenyl- or alkoxyalkenyl-such as $C_1$-$C_3$-alkyl-O—($C_2$-$C_4$-alkenyl)-, the substituents can be present in any desired position.

Examples of $C_3$-$C_5$-alkandiyl are —$CH_2CH_2CH_2$—, —$CH_2$—$CH(CH_3)$—, —$CH_2CH_2CH_2CH_2$— and —$CH_2CH_2CH_2CH_2CH_2$— groups.

If not stated otherwise, the above-mentioned phenyl residues, naphthyl and indanyl residues and heterocyclic residues (including heteroaryl residues) can be unsubstituted or can carry one or more, for example 1, 2, 3 or 4, of the substituents indicated in the above definition which substituents can be present in any desired position. If in compounds of the formula I nitro groups are present as substituents, in a preferred embodiment of the invention in total only up to two nitro groups are present in the molecule. In monosubstituted phenyl residues the substituent can be in the 2-position, the 3-position or the 4-position, in disubstituted phenyl residues the substituents can be in 2,3-position, 2,4-position, 2,5-position, 2,6-position, 3,4-position or 3,5-position. In trisubstituted phenyl residues the substituents can be in 2,3,4-position, 2,3,5-position, 2,3,6-position, 2,4,5-position, 2,4,6-position or 3,4,5-position. In fourfold substituted phenyl residues, the substituents can be in the 2,3,4,5-position, the 2,3,4,6-position, or the 2,3,5,6-position. Tolyl (=methylphenyl) can be 2-tolyl, 3-tolyl or 4-tolyl. Naphthyl can be 1-naphthyl or 2-naphthyl. In monosubstituted 1-naphthyl residues the substituent can be in the 2-position, the 3-position, the 4-position, the 5-position, the 6-position, the 7-position or the 8-position, in monosubstituted 2-naphthyl residues in the 1-position, the 3-position, the 4-position, the 5-position, the 6-position, the 7-position or the 8-position. In higher substituted naphthyl residues, for example 1-naphthyl residues or 2-naphthyl residues which carry two or three substituents, the substituents can be present in any desired positions. Indanyl residues include indan-1-yl residues and indan-2-yl residues which can be unsubstituted or carry one or more of the substituents indicated. In case the indanyl residues are substituted, the substituent or substituents can be present in any of the positions possible.

Unless stated otherwise, heteroaryl residues and heterocyclic residues are preferably derived from heterocycles which contain 1, 2, 3 or 4 heteroatoms which can be identical or different; more preferably they are derived from heterocycles which contain 1, 2 or 3, in particular 1 or 2, heteroatoms which can be identical or different. Unless stated otherwise, the heterocycles can be monocyclic or polycyclic, for example monocyclic, bicyclic or tricyclic. Preferably they are monocyclic or bicyclic.

The number of ring members preferably is 5, 6, 8, 9 or 10. The individual rings preferably are 5-membered rings, 6-membered rings or 7-membered rings. Examples of monocyclic and bicyclic heterocyclic systems from which residues occurring in the compounds of the formula I can be derived, are pyrrole, furan, thiophene, imidazole, pyrazole, 1,2,3-triazole, 1,2,4-triazole, 1,3-dioxole, 1,3-oxazole (=Oxazole), 1,2-oxazole (=isoxazole), 1,3-thiazole (=thiazole), 1,2-thiazole (=isothiazole), tetrazole, pyridine, pyridazine, pyrimidine, pyrazine, pyran, thiopyran, 1,4-dioxine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, 1,2,4,5-tetrazine, azepine, 1,2-diazepine, 1,3-diazepine, 1,4-diazepine, 1,3-oxazepine, 1,3-thiazepine, indole, benzothiophene, benzofuran, benzothiazole, benzoxazole, benzimidazole, benzodioxole, quinoline, isoquinoline, cinnoline, quinazoline, quinoxaline, phthalazine, thienothiophenes, 1,8-naphthyridine and other naphthyridines, pteridin, or phenothiazine, each of them in saturated form (perhydro form) or in partially unsaturated form (for example in the dihydro form or the tetrahydro form) or in maximally unsaturated form or aromatic form, provided that the respective forms are known and stable. The term "aryl" and the term "heteroaryl" as used herein comprise bicyclic residues in which both cycles are aromatic as well as bicyclic residues in which only one cycle is aromatic. The same applies to the term "group Ar" or the term "group Hetar". Suitable heterocycles include, for example, the saturated heterocycles pyrrolidine, piperidine, piperazine, morpholine and thiomorpholine. The degree of saturation of heterocyclic groups is indicated in their individual definitions. Unsaturated heterocycles can contain, for example, 1, 2 or 3, double bonds within the ring system. 5-membered rings and 6-membered rings can in particular also be aromatic.

Residues derived from the mentioned heterocycles can be attached via any suitable carbon atom. Residues derived from nitrogen heterocycles which can carry a hydrogen atom or a substituent on a ring nitrogen atom, such as pyrrole, imidazole, pyrrolidine, morpholine or piperazine residues, can also be attached via a ring nitrogen atom, in particular if the respective heterocyclic residue is attached to a carbon atom. For example, a thienyl residue can be present as 2-thienyl residue or 3-thienyl residue, a furyl residue as 2-furyl residue or 3-furyl residue, a pyridinyl residue as 2-pyridinyl residue, 3-pyridinyl residue or 4-pyridinyl residue, a piperidinyl residue as 1-piperidinyl residue (=piperidino residue), 2-piperidinyl residue, 3-piperidinyl residue or 4-piperidinyl residue, a (thio)morpholinyl residue as 2-(thio)

morpholinyl residue, 3-(thio)morpholinyl residue or 4-(thio) morpholinyl residue (=thiomorpholino residue). A residue derived from 1,3-thiazole or imidazole which is attached via a carbon atom can be attached via the 2-position, the 4-position or the 5-position.

In case a heterocyclic groups is substituted, it can carry one or more, for example 1, 2, 3 or 4, identical or different substituents. Substituents in heterocycles can be present in any desired positions, for example in a 2-thienyl residue or 2-furyl residue in the 3-position and/or in the 4-position and/or in the 5-position, in a 3-thienyl residue or 3-furyl residue in the 2-position and/or in the 4-position and/or in the 5-position, in a 2-pyridinyl residue in the 3-position and/or in the 4-position and/or in the 5-position and/or in the 6-position, in a 3-pyridinyl residue in the 2-position and/or in the 4-position and/or in the 5-position and/or in the 6-position, in a 4-pyridinyl residue in the 2-position and/or in the 3-position and/or in the 5-position and/or in the 6-position. Suitable nitrogen heterocycles can also be present as N-oxides or as quarternary salts containing a counterion that is derived from a pharmaceutically acceptable acid. Pyridine moieties, for example, can thus be present as pyridine-N-oxides.

Halogen is fluorine, chlorine, bromine or iodine, preferably fluorine or chlorine.

Patient includes both human and other mammals.

Pharmaceutically effective amount means an amount of the compound according to the invention effective in producing the desired therapeutic effect.

Particular or Preferred Embodiments

In preferred embodiments of the present invention, one or more of the structural moieties in the compounds of formula I, including the groups X, $R^1$, $R^2$, $R^3$, $R^4$, $R^5$ and the other groups present in the compounds of formula I, independently from each other have the following preferred meanings, more preferred meanings, even more preferred meanings or most preferred meanings.

$R^1$ is preferably selected from the group consisting of: H; $C_1$-$C_4$-alkyl; $C_1$-$C_4$-alkoxy; $CF_3$; halogen; —CN; $C_1$-$C_4$-alkyl-$S(O)_m$—; and unsubstituted and at least monosubstituted phenyl and heteroaryl the substituents of which are selected from the group consisting of halogen, —CN, $C_1$-$C_3$-alkyl, $C_1$-$C_3$-alkoxy and $CF_3$, where heteroaryl is selected from the group consisting of 5-membered and 6-membered heterocycles containing one or more heteroatoms selected from the group consisting of N, O, and S. More preferably $R^1$ is H, halogen or $C_1$-$C_4$-alkyl.

$R^2$ is preferably selected from the group consisting of H, halogen, —CN and $C_1$-$C_4$-alkyl, more preferably from the group consisting of H, halogen and $C_1$-$C_4$-alkyl. Even more preferably $R^2$ is H.

$R^3$ is preferably selected from the group consisting of H, halogen, —CN and $C_1$-$C_4$-alkyl, more preferably from the group consisting of H, halogen and $C_1$-$C_4$-alkyl. Even more preferably $R^3$ is H.

$R^4$ is preferably selected from the group consisting of: H; $C_1$-$C_4$-alkyl; $C_1$-$C_4$-alkoxy; $CF_3$; halogen; —CN; $C_1$-$C_4$-alkyl-$S(O)_m$—; and unsubstituted and at least monosubstituted phenyl and heteroaryl the substituents of which are selected from the group consisting of halogen, —CN, $C_1$-$C_3$-alkyl, $C_1$-$C_3$-alkoxy and $CF_3$, where heteroaryl is selected from the group consisting of 5-membered and 6-membered heterocycles containing one or more heteroatoms selected from the group consisting of N, O, and S. More preferably $R^4$ is H, halogen or $C_1$-$C_4$-alkyl. Most preferably $R^4$ is H.

In a preferred embodiment of the present invention $R^1$, $R^2$, $R^3$ and $R^4$ are all H. In another preferred embodiment of the invention the group X is $NR^{30}$ and at least one of the groups $R^1$, $R^2$, $R^3$ and $R^4$, for example one or two of them, is different from hydrogen.

$R^5$ is preferably a group Ar or a group Hetar both of which are unsubstituted or carry one or more identical or different substituents selected from the group consisting of: halogen; —CN; $NH_2$; unsubstituted and at least monosubstituted $C_1$-$C_8$-alkyl, $C_2$-$C_8$-alkenyl, $C_2$-$C_8$-alkynyl, $C_1$-$C_8$-alkoxy, $C_1$-$C_8$-alkylamino and di($C_1$-$C_8$-alkyl)amino, the substituents of which are selected from the group consisting of F, OH, $C_1$-$C_6$-alkoxy, phenoxy, $C_1$-$C_6$-alkylmercapto, $NH_2$, $C_1$-$C_6$-alkylamino and di($C_1$-$C_6$-alkyl)amino; $C_3$-$C_5$-alkandiyl; phenyl; heteroaryl;-phenyl-substituted or heteroaryl-substituted $C_1$-$C_2$-alkyl; $CF_3$; OH; phenoxy; benzyloxy; ($C_1$-$C_6$-alkyl)-COO; $S(O)_m$—($C_1$-$C_6$)-alkyl which can optionally be substituted by OH or $C_1$-$C_6$-alkoxy; $S(O)_m$-phenyl; $S(O)_m$-heteroaryl; SH; phenylamino; benzylamino; ($C_1$-$C_6$-alkyl)-CONH—; ($C_1$-$C_6$-alkyl)-CON($C_1$-$C_4$-alkyl)-; phenyl-CONH—; phenyl-CON($C_1$-$C_4$-alkyl)-; heteroaryl-CONH—; heteroaryl-CON($C_1$-$C_4$-alkyl)-; ($C_1$-$C_6$-alkyl)-CO—; phenyl-CO—; heteroaryl-CO—; $CF_3$—CO—; —$OCH_2O$—; —$OCF_2O$—; —$OCH_2CH_2O$—; —$CH_2CH_2O$—; COO($C_1$-$C_6$-alkyl); —$CONH_2$; —CONH($C_1$-$C_6$-alkyl); —CON(di($C_1$-$C_6$-alkyl)); C(NH)—$NH_2$; —$SO_2NH_2$; —$SO_2NH$($C_1$-$C_6$-alkyl); —$SO_2NH$(phenyl); —$SO_2N$(di($C_1$-$C_6$-alkyl)); ($C_1$-$C_6$-alkyl)-$SO_2NH$—; ($C_1$-$C_6$-alkyl)-$SO_2N$($C_1$-$C_6$-alkyl)-; phenyl-$SO_2NH$—; phenyl-$SO_2N$($C_1$-$C_6$-alkyl)-; heteroaryl-$SO_2NH$—; heteroaryl-$SO_2N$($C_1$-$C_6$-alkyl)-; and a residue of a saturated or at least monounsaturated aliphatic, mononuclear 5-membered to 7-membered heterocycle containing 1, 2 or 3 heteroatoms selected from the group consisting of N, O and S, which heterocycle can be substituted by one or more substituents selected from the group consisting of halogen, $C_1$-$C_3$-alkyl, $C_1$-$C_3$-alkoxy, OH, oxo and $CF_3$, where said heterocycle can optionally be condensed to the said group Ar or the said group Hetar; wherein all heteroaryl, phenyl, heteroaryl-containing and phenyl-containing groups, which are optionally present in the said substituents of the said group Ar or the said group Hetar, can be substituted by one or more substituents selected from the group consisting of halogen, —CN, $C_1$-$C_3$-alkyl, OH, $C_1$-$C_3$-alkoxy, and $CF_3$;

$R^5$ is more preferably phenyl or a group Hetar both of which are unsubstituted or carry one or more identical or different substituents selected from the group consisting of: halogen; —CN; $NH_2$; unsubstituted and at least monosubstituted $C_1$-$C_6$-alkyl, $C_2$-$C_6$-alkenyl, $C_2$-$C_6$-alkynyl, $C_1$-$C_3$-alkoxy, $C_1$-$C_4$-alkylamino and di($C_1$-$C_4$-alkyl)amino, the substituents of which are selected from the group consisting of F, $C_1$-$C_3$-alkoxy, $C_1$-$C_3$-alkylmercapto and $NH_2$; $C_3$-$C_5$-alkandiyl; phenyl; heteroaryl; phenyl-substituted or heteroaryl-substituted $C_1$-$C_2$-alkyl; $CF_3$; OH; ($C_1$-$C_4$-alkyl)-COO; $S(O)_m$-($C_1$-$C_4$)-alkyl; ($C_1$-$C_4$-alkyl)-CONH—; ($C_1$-$C_4$-alkyl)—CON($C_1$-$C_4$-alkyl)-; ($C_1$-$C_4$-alkyl)-CO—; phenyl-CO—; heteroaryl-CO—; $CF_3$—CO—; —$OCH_2O$—; —$OCF_2O$—; —$OCH_2CH_2O$—; —$CH_2CH_2O$—; COO($C_1$-$C_6$-alkyl); —$CONH_2$; —CONH($C_1$-$C_4$-alkyl); —CON(di($C_1$-$C_4$-alkyl)); C(NH)$NH_2$; —$SO_2NH_2$; —$SO_2NH$($C_1$-$C_4$-alkyl); —$SO_2NH$(phenyl); —$SO_2N$(di($C_1$-$C_4$-alkyl)); ($C_1$-$C_4$-alkyl)-$SO_2NH$—; ($C_1$-$C_4$-alkyl)-$SO_2N$($C_1$-$C_4$-alkyl)-; and a residue of a saturated or at least monounsaturated aliphatic, mononuclear 5-membered to 7-membered heterocycle containing 1, 2 or 3 heteroatoms selected from the group consisting of N, O and S, which heterocycle can be substituted by one or more substituents selected from the group consisting of halogen, $C_1$-$C_3$-alkyl, $C_1$-$C_3$-alkoxy, OH, oxo and $CF_3$, where said heterocycle can optionally be condensed to the said phenyl or the said group Hetar; wherein all heteroaryl, phenyl, heteroaryl-containing and phenyl-containing groups, which are optionally present in the said substituents of the said phenyl or the said group Hetar, can be substituted by one or more substituents selected from the group consisting of halogen, —CN, $C_1$-$C_3$-alkyl, OH, $C_1$-$C_3$-alkoxy, and $CF_3$.

$R^5$ is even more preferably phenyl or a group Hetar both of which are unsubstituted or carry one or more identical or different substituents selected from the group consisting of: F; Cl; Br; $C_1$-$C_3$-alkyl; $C_1$-$C_3$-alkoxymethyl; 2-amino-3,3,3-trifluoropropyl-; $CF_3$; $C_3$-$C_5$-alkandiyl; phenyl; heteroaryl; benzyl; heteroaryl-methyl-; OH; $C_1$-$C_3$-alkoxy; phenoxy; trifluoromethoxy; 2,2,2-trifluoroethoxy; ($C_1$-$C_4$-alkyl)-COO; $C_1$-$C_3$-alkylmercapto; phenylmercapto; $C_1$-$C_3$-alkylsulfonyl; phenylsulfonyl; $NH_2$; $C_1$-$C_4$-alkylamino; di($C_1$-$C_4$-alkyl)amino; ($C_1$-$C_3$-alkyl)-CONH—; ($C_1$-$C_3$-alkyl)-$SO_2$NH—; ($C_1$-$C_3$-alkyl)-CO—; phenyl-CO—; —$OCH_2$O—; —$OCF_2$O—; —$CH_2CH_2$O—; COO ($C_1$-$C_4$-alkyl); —$CONH_2$; —CONH($C_1$-$C_4$-alkyl); —CON(di($C_1$-$C_4$-alkyl)); —CN; —$SO_2NH_2$; —$SO_2$NH ($C_1$-$C_4$-alkyl); —$SO_2$N(di($C_1$-$C_4$-alkyl)); pyrrolidinyl; piperidinyl; morpholinyl and thiomorpholinyl; wherein all heteroaryl, phenyl, heteroaryl-containing and phenyl-containing groups, which are optionally present in the said substituents of the said phenyl or the said group Hetar, can be substituted by one or more substituents selected from the group consisting of halogen, —CN, $C_1$-$C_3$-alkyl, OH, $C_1$-$C_3$-alkoxy, and $CF_3$.

$R^5$ is most preferably selected from the group consisting of 4-fluorophenyl, 4-chlorophenyl, 4-bromophenyl, 4-($C_1$-$C_3$-alkoxy)-phenyl, 4-trifluoromethoxyphenyl, 2-bromo-4-fluorophenyl, 2-chloro-4-fluorophenyl, 3,4-dimethylphenyl, 2,4-dimethylphenyl, 4-chloro-2-methylphenyl, 2-hydroxy-4-methylphenyl, 2-hydroxy-4-ethoxyphenyl, 2-methoxy-4-methylphenyl, 4-phenoxyphenyl, 3-fluoro-4-methylphenyl, benzo[1,3]dioxol-5-yl, 2,2-difluorobenzo[1,3]dioxol-5-yl, 2,3-dihydrobenzofuran-5-yl, 1-(4-chlorophenyl)-5-trifluoromethyl-1H-pyrazol-4-yl, 1-(4-fluorophenyl)-3,5-dimethyl-1H-pyrazol-4-yl, 1H-benzotriazol-5-yl, 1H-indol-4-yl, 1H-indol-6-yl, 1-isopropyl-2-trifluoromethyl-1H-benzimidazol-5-yl, 1-methyl-3-oxo-1,2,3,4-tetrahydro-quinoxalin-6-yl, 1-phenyl-5-trifluoromethyl-1H-pyrazol-4-yl, 2-(2-hydroxypyridin-4-yl)-1H-benzimidazol-5-yl, 2-(4-cyanophenyl)-1H-benzimidazol-5-yl, 2,4-dimethyloxazol-5-yl, 2,4-dimethylpyrimidin-5-yl, 2,4-dimethylthiazol-5-yl, 2,5-dimethyl-1H-pyrrol-3-yl, 2,5-dimethyl-1-phenyl-1H-pyrrol-3-yl, 2,5-dimethyl-1-(pyridin-4-ylmethyl)-1H-pyrrol-3-yl, 2,5-dimethyl-2H-pyrazol-3-yl, 2,6-dichloropyridin-3-yl, 2,6-dimethoxypyridin-3-yl, 2,6-dimethylpyridin-3-yl, 2-amino-4,6-dimethylpyridin-3-yl, 2-amino-6-chloropyridin-3-yl, 2-aminopyridin-3-yl, 2-chloro-6-methylpyridin-3-yl, 2-chloropyridin-4-yl, 2-cyclopropyl-4-methylthiazol-5-yl, 2-dimethylamino-4-methylthiazol-5-yl, 2-dimethylaminopyridin-4-yl, 2-ethyl-5-methyl-2H-pyrazol-3-yl, 2-hydroxy-6-methylpyridin-3-yl, 2-methyl-1H-benzimidazol-5-yl, 2-methyl-3H-benzimidazol-5-yl, 2-methylpyridin-3-yl, 2-methyl-6-trifluoromethylpyridin-3-yl, 2-methylthiazol-5-yl, 2-(morpholin-4-yl)-pyridin-4-yl, 2-(morpholin-4-yl)-pyrimidin-5-yl, 2-(pyrrolidin-1-yl)-pyridin-4-yl, 3,5-dimethyl-1H-pyrazol-4-yl, 3-amino-5,6-dimethylpyrazin-2-yl, 3-amino-5-methylpyrazin-2-yl, 3-aminopyrazin-2-yl, 3-dimethylamino-4-methylphenyl, 3-dimethylaminophenyl, 3H-benzimidazol-5-yl, 1H-benzimidazol-5-yl, 3-methylsulfonylamino-2-methylphenyl, 3-methylsulfonylaminophenyl, 3-methylisoxazol-4-yl, 3-(morpholin-4-yl)-phenyl, 3-(piperidin-1-yl)-phenyl, 3-(pyrrolidin-1-yl)-phenyl, 4-(2,2,2-trifluoroethoxy)phenyl, 4,6-dimethylpyridin-3-yl, 4-amino-2-ethylsulfanylpyrimidin-5-yl, 4-amino-2-methylpyrimidin-5-yl, 4-chloro-3-methylsulfonylaminophenyl, 4-chloro-3-sulfamoylphenyl, 4-methyl-3-methylaminophenyl, 4-methylthiazol-5-yl, pyridin-2-yl, 5,6,7,8-tetrahydroquinolin-3-yl, 5-amino-1-phenyl-1H-pyrazol-4-yl, 5-methylsulfonyl-2-methylphenyl, 5-methyl-1-phenyl-1H-pyrazol-4-yl, 5-methylisoxazol-3-yl, 5-methylpyridin-3-yl, 5-methylpyrazin-2-yl, 6-chloropyridin-3-yl, 6-cyanopyridin-3-yl, 6-dimethylaminopyridin-3-yl, 6-ethynylpyridin-3-yl, 6-methoxymethylpyridin-3-yl, 6-methoxypyridin-3-yl, 6-methyl-2-methylaminopyridin-3-yl, 6-methylaminopyrazin-2-yl, 6-methylpyridin-3-yl, 6-(morpholin-4-yl)-pyridin-3-yl, 6-(pyrrolidin-1-yl)-pyridin-3-yl, imidazo[1,2-a]pyridin-2-yl, 6-trifluoromethylpyridin-3-yl, pyrimidin-4-yl, 4-methylsulfanylphenyl, 4-ethylsulfanylphenyl, 3-methoxycarbonylphenyl, 4-methoxycarbonylphenyl, 3-ethoxycarbonylphenyl, 4-ethoxycarbonylphenyl, 2-bromo-4-chlorophenyl, 2,3-dichlorophenyl, 3-chloro-4-(isopropylsulfonyl)thiophen-2-yl, 4-bromo-2-chlorophenyl, 4-methoxyphenyl, 4-ethoxyphenyl, 3-methoxyphenyl, 3-ethoxyphenyl, 2-methyl-thiophen-3-yl, 3-chloro-4-methyl-thiophen-2-yl, 5-bromo-thiophen-2-yl, 5-chloro-thiophen-2-yl, 5-methyl-thiophen-2-yl, 4-methyl-thiophen-2-yl, 3-methyl-thiophen-2-yl, 5-acetyl-thiophen-2-yl, pyridin-3-yl, pyridin-4-yl, 4-trifluoromethylphenyl, 4-ethylaminophenyl, 4-methylaminophenyl, 2-aminophenyl, 4-bromo-2-fluorophenyl, 2-chlorophenyl, 3-chloro-4-methylphenyl, 4-chloro-3-methylphenyl, 2-chloro-3-methylphenyl, 2-methylphenyl, 2-acetoxy-4-methylphenyl, 2-acetoxy-4-ethoxyphenyl, 2-acetoxy-4-methoxyphenyl, 4-trifluoromethylsulfanylphenyl, naphthalen-2-yl, 1,1-dimethylindan-4-yl, 3-isobutyrylaminophenyl, 3-(2,2-dimethylpropionylamino)phenyl, 2-bromophenyl, 2-fluorophenyl, 3-bromo-5-methylthiophen-2-yl, 3-chloro-6-fluorobenzo[b]thiophen-2-yl and 3,4-dichlorobenzo[b]thiophen-2-yl.

$R^{30}$ is preferably is selected from the group consisting of: H; unsubstituted and at least monosubstituted $C_1$-$C_6$-alkyl the substituents of which are selected from the group consisting of F, OH, $C_1$-$C_8$-alkoxy and unsubstituted and at least monosubstituted phenyl and heteroaryl where the substituents of the phenyl and monocyclic heteroaryl groups are selected from the group consisting of halogen, $C_1$-$C_3$-alkyl, $C_1$-$C_3$-alkoxy and $CF_3$; and unsubstituted and at least monosubstituted phenyl the substituents of which are selected from the group consisting of halogen, $C_1$-$C_3$-alkyl, $C_1$-$C_3$-alkoxy and $CF_3$. More preferably $R^{30}$ is selected from the group consisting of H and unsubstituted $C_1$-$C_4$-alkyl, even more preferably from the group consisting of H and methyl. Most preferably $R^{30}$ is methyl.

In a preferred embodiment of the invention X is $NR^{30}$, S or CH═CH, in a more preferred embodiment X is $NR^{30}$ or S, in an even more preferred embodiment X is $NR^{30}$, where in all these embodiments $R^{30}$ preferably is hydrogen or methyl and more preferably is methyl. In another preferred embodiment of the invention X is $NR^{30}$, O or S, preferably $NR^{30}$ or S, more preferably $NR^{30}$, the heteroaromatic ring comprising the group X thus being a 5-membered ring and the encompassed compounds being 2-acylaminobenzimidazole derivatives of the formula Ia, 2-acylaminobenzoxazole derivatives of the formula Ib or 2-acylaminobenzothiazole derivatives of the formula Ic, respectively. In a further preferred embodiment of the invention X is CH═CH, N═CH or CH═N, preferably CH═CH, the heteroaromatic ring comprising the group X thus being a 6-membered ring and the encompassed compounds being 2-acylaminoquinoline derivatives of the formula Id, 2-acylaminoquinoxalines derivatives of the formula Ie or 2-acylaminoquinazoline derivatives of the formula If, respectively.

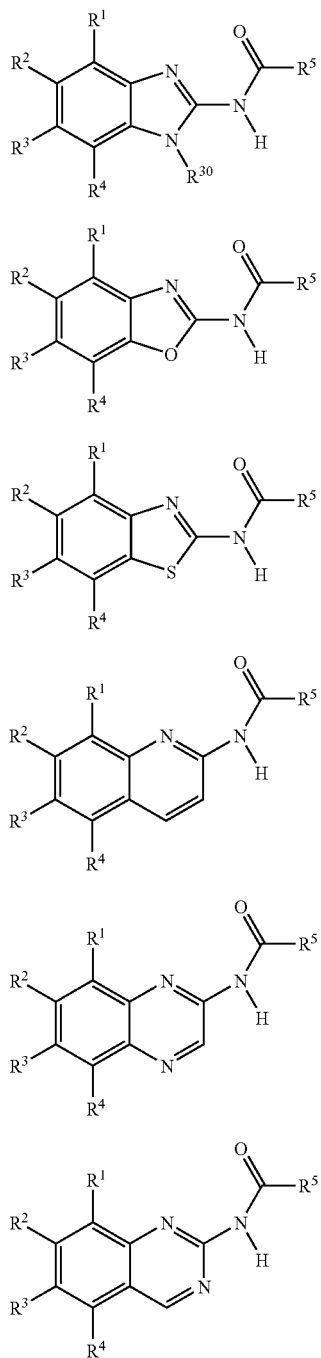

In the compounds of formula Ia to If the groups $R^1$, $R^2$, $R^3$, $R^4$ and $R^5$ can have any of the general or preferred or more preferred etc. meanings or of the specific meanings mentioned above or below. For example, in the compounds of the formula Ia the group $R^{30}$ can have the general meaning of $R^{30}$ or a preferred meaning including hydrogen and methyl.

Heteroaryl is preferably a residue of 5-membered to 10-membered, aromatic, monocyclic or bicyclic heterocycle containing 1, 2 or 3 heteroatoms selected from the group consisting of N, O and S. More preferably heteroaryl is selected from the group consisting of furyl, pyrrolyl, thienyl, thiazolyl, isothiazolyl, oxazolyl, isoxazolyl, pyrazolyl, imidazolyl, pyridazinyl, pyrazinyl, pyridinyl, pyrimidinyl, benzimidazolyl, benzothiazolyl, benzoxazolyl, quinolinyl, isoquinolinyl, quinoxalinyl, quinazolinyl, indolyl, benzofuranyl, benzodioxolyl, benzothiophenyl and indazolyl.

The group Hetar is preferably a residue of a 5-membered to 10-membered, aromatic, mono- or bicyclic heterocycle containing 1, 2 or 3 heteroatoms selected from the group consisting of N, O and S. More preferably the group Hetar is selected from the group consisting of furyl, pyrrolyl, thienyl, thiazolyl, isothiazolyl, oxazolyl, isoxazolyl, pyrazolyl, imidazolyl, pyridazinyl, pyrazinyl, pyridinyl, pyrimidinyl, benzimidazolyl, benzothiazolyl, benzoxazolyl, quinolinyl, isoquinolinyl, quinoxalinyl, quinazolinyl, indolyl, benzofuranyl, benzodioxolyl, benzothiophenyl and indazolyl.

Aryl is preferably phenyl.

m is preferably 0 or 2.

Preferred compounds of the formula I are those compounds in which one or some or all of the structural moieties and groups contained therein have preferred meanings, more preferred meanings, even more preferred meanings or most preferred meanings defined above, all combinations of such preferred meanings etc. and/or of specific meanings of a group being a subject of the present invention. With respect to all preferred compounds of the formula I the present invention also includes all stereoisomeric forms and mixtures thereof in all ratios, and their pharmaceutically acceptable salts.

The invention also encompasses all combinations of particular and preferred aspects of the invention noted herein.

The present invention includes all stereoisomeric forms of the compounds of the formula I. Centers of asymmetry that are present in the compounds of formula I all independently from one another can have S configuration or R configuration. The invention includes all possible enantiomers and diastereomers and mixtures of two or more stereoisomers, for example mixtures of enantiomers and/or diastereomers, in all ratios. Thus, compounds of the present invention that can exist as enantiomers can be present in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. All these forms are a subject of the present invention. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at the stage of the compounds of the formula I or at the stage of an intermediate during the synthesis or at the stage of a starting compound. The present invention also includes all tautomeric forms of the compounds of formula I.

In case the compounds of the formula I contain one or more acidic or basic groups, the invention also comprises their corresponding pharmaceutically or toxicologically acceptable salts, in particular their pharmaceutically utilizable salts. Thus, the compounds of the formula I that contain acidic groups can be present on these groups and can be used according to the invention, for example, as alkali metal salts, alkaline earth metal salts or as ammonium salts. Examples of such salts include sodium salts, potassium salts, calcium salts, magnesium salts or salts with ammonia or organic amines such as, for example, ethylamine, ethanolamine, triethanolamine or amino acids. Compounds of the formula I which contain one or more basic groups, i.e. groups which can be protonated, can be present and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid, and other acids known to the person skilled in the art. If the compounds of the formula I simultaneously contain acidic and basic groups in the molecule, the invention also includes, in addition to the salt forms mentioned, inner salts or betaines (zwitterions). The salts of the compounds of the formula I can be obtained by customary methods which are known to the person skilled in the art like, for example, by contacting the compound of the formula I with an organic or inorganic acid or base in a solvent or diluent, or by anion exchange or cation exchange from another salts. The present invention also includes all salts of the compounds of the formula I which, owing to low physiological compatibility, are not directly suitable for use in pharmaceuticals but which can be used, for example, as intermediates for chemical reactions or for the preparation of pharmaceutically acceptable salts. The present invention furthermore includes all solvates of compounds of the formula I, for example hydrates and adducts with alcohols, active metabolites of the compounds of the formula I, and also derivatives and prodrugs of the compounds of the formula I which contain physiologically tolerable and cleavable groups, for example esters, amides and compounds in which the N—H group depicted in formula I is replaced with an N-alkyl group, such as N-methyl, or with an N-acyl group, such as N-acetyl or N-argininyl, including pharmaceutically acceptable salts formed on functional groups present in the N-acyl group.

A compound of the formula I or a salt thereof can be prepared, for example, by a process which comprises the acylation of a heteroaromatic amine of the formula II with a carboxylic acid of the formula $R^5$—COOH or a derivative thereof, which process also is a subject of the present invention.

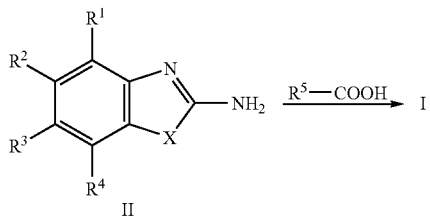

Suitable derivatives of the carboxylic acids of the formula $R^5$—COOH are, for example, carboxylic acid chlorides, esters including $C_1$-$C_4$-alkyl esters, such as methyl esters or ethyl esters, optionally substituted aryl esters, such as phenyl esters or nitrophenyl esters, or activated esters, or anhydrides or mixed anhydrides. In the compounds of the formula II and the carboxylic acids of the formula $R^5$—COOH and their derivatives the groups X, $R^1$, $R^2$, $R^3$, $R^4$ and $R^5$ have the meanings indicated above with respect to the compounds of the formula I, or else functional groups can be present in protected form or in the form of a precursor. For example, when a compound of the formula I is to be prepared which contains a carboxylic acid group or an amino group, it may be appropriate that in the acylation reaction these groups are present in protected form, for example as an ester such as a tert-butyl ester or benzyl ester instead of the free carboxylic acid group, or as an acylated amino group such as a tert-butoxycarbonylamino group or benzyloxycarbonylamino group instead of the free amino group, and only subsequent to the acylation the desired final groups are liberated by deprotection. Suitable protective group strategies that may be used in the synthesis of the compounds of formula I are known to the person skilled in the art. An example of a precursor group of a functional group is the nitro group which can be converted into an amino group by reduction, for example by catalytic hydrogenation, after the acylation reaction.

The acylation reactions can be carried out under standard conditions known to the person skilled in the art. In many cases the reaction is favorably performed in an inert solvent or diluent, for example a hydrocarbon or a chlorinated hydrocarbon, such as toluene, 1,2-dichloroethane or methylene chloride, an ether, such as tetrahydrofuran, dioxane or 1,2-dimethoxyethane, an alcohol such as methanol, ethanol or isopropanol, an amide such as N,N-dimethylformamide or N-methylpyrrolidone, acetonitrile, water, or a else a mixture of two or more solvents or diluents. Depending on the individual case, it may be advantageous to perform the reaction in the presence of a base, for example an inorganic base such as sodium hydroxide, sodium carbonate or sodium hydrogencarbonate, or an organic base such as triethylamine, ethyldiisopropylamine, N-ethylmorpholine or pyridine, and/or in the presence of an acylation catalyst such as 4-dimethylaminopyridine.

If a carboxylic acid of the formula $R^5$—COOH is to be used in the acylation of a compound of the formula II, it is often advantageous to activate the acid or a salt thereof with a condensation agent or coupling agent, for example an agent like those commonly used in peptide chemistry for the formation of amide bonds. Examples of suitable coupling agents are carbodiimides such as dicyclohexylcarbodiimide or diisopropylcarbodiimide, TOTU, i.e. O-((cyano(ethoxycarbonyl)methylene)amino)-N,N,N',N'-tetramethyluronium tetrafluoroborate, HATU, i.e. O-(7-azabenzotriazol-1-yl)-1,1,3,3-tetramethyluronium hexafluorophosphate, chloroformic acid esters like ethyl chloroformate or isobutyl chloroformate, tosyl chloride, propylphosphonic acid anhydride or carbonyldiimidazole. Depending on the individual case, the suitable reaction temperature may lie within a wide range. For example, when employing into the acylation reaction a carboxylic acid in the presence of a coupling agent or a carboxylic acid chloride, the reaction can often be carried out at room temperature.

Subsequent to the acylation reaction, besides the above-mentioned deprotection of protected groups or the conversion of a precursor group into the desired final group, optionally further functionalizations or modifications of the obtained compounds can be carried out and suitable functional groups can, for example, be esterified, amidated, transesterified, hydrolyzed, alkylated, sulfonylated, acylated, reduced, oxidized, converted into a salt, or subjected to other reactions.

The starting compounds for the preparation of the compounds of the formula I are commercially available or can be prepared according to or analogously to literature procedures. All reactions for the synthesis of the compounds of the formula I are per se well-known to the skilled person and can be carried out under standard conditions according to or analogously to procedures described in the literature, for example in Houben-Weyl, Methoden der Organischen Chemie (Methods of Organic Chemistry), Thieme-Verlag, Stuttgart, or Organic Reactions, John Wiley & Sons, New York (the content of which is incorporated herein by reference). As mentioned above, depending on the circumstances of the individual case, in order to avoid side reactions during the synthesis of a compound of the formula I, in any reaction step it can be necessary or advantageous to temporarily block functional groups by introducing protective groups and to deprotect them in a later stage of the synthesis, or introduce functional groups in the form of precursor groups which in a later reaction step are converted into the desired functional groups. Such synthesis strategies and protective groups and precursor groups which are suitable in an individual case are known to the skilled person. If desired, the compounds of the formula I can be purified by customary purification procedures, for example by recrystallization or chromatography.

The compounds of the formula I are useful pharmaceutically active compounds which upregulate the expression of endothelial NO synthase and can be employed as medicaments for the treatment of various diseases. In the context of the present invention, treatment is understood as comprising both therapy, including alleviation and cure, of disease symptoms and prevention or prophylaxis of disease symptoms, such as, for example, the prevention of the appearance of asthmatic disease symptoms or the prevention of myocardial infarction or of myocardial reinfarction in relevant patients. The diseases or disease symptoms can be acute or chronic. Diseases which can be treated with the compounds of the formula I include, for example, cardiovascular diseases like stable and unstable angina pectoris, coronary heart disease, Prinzmetal angina (spasm), acute coronary syndrome, heart failure, myocardial infarction, stroke, thrombosis, peripheral artery occlusive disease (PAOD), endothelial dysfunction, atherosclerosis, restenosis, endothel damage after PTCA, hypertension including essential hypertension, pulmonary hypertension and secondary hypertension (renovascular hypertension, chronic glomerulonephritis), erectile dysfunction and ventricular arrhythmia. Further, the compounds of the formula I lower the cardiovascular risk of postmenopausal women and of women taking contraceptives. Compounds of the formula I can additionally be used in the treatment, i.e. the therapy and prevention, of diabetes and diabetes complications (nephropathy, retinopathy), angiogenesis, asthma bronchiale, chronic renal failure, cirrhosis of the liver, osteoporosis, restricted memory performance or a restricted ability to learn. Preferred indications are stable angina pectoris, coronary heart disease, hypertension, endothelial dysfunction, atherosclerosis and diabetes complications.

The compounds of the formula I can be used in combination with other pharmaceutically active compounds, preferably with compounds which are able to enhance the effect of the compounds of the formula I. Examples of such other compounds include statins; ACE inhibitors; AT1 antagonists; argininase inhibitors; PDE V inhibitors; calcium antagonists; alpha blockers; beta blockers; thiamazole (methimazole) and analogous compounds; arginine; tetrahydrobiopterin; vitamins, in particular vitamin C and vitamin B6; niacine.

The compounds of the formula I and their pharmaceutically acceptable salts, optionally in combination with other pharmaceutically active compounds, can be administered to animals, preferably to mammals, and in particular to humans, as pharmaceuticals by themselves, in mixtures with one another or in the form of pharmaceutical preparations. Further subjects of the present invention therefore also are the compounds of the formula I and their pharmaceutically acceptable salts for use as pharmaceuticals, their use as transcription stimulating agents or upregulating agents of endothelial NO synthase, for example in conditions in which an increased expression of said enzyme or an increased NO level or the normalization of a decreased NO level in a patient is desired, and in particular their use in the treatment, i.e. the therapy and prevention, of the above-mentioned syndromes, as well as their use for preparing medicaments for these purposes. Furthermore, a subject of the present invention are pharmaceutical preparations (or pharmaceutical compositions) which comprise an effective dose of at least one compound of the formula I and/or a pharmaceutically acceptable salt thereof and a pharmaceutically acceptable carrier, i.e. one or more pharmaceutically acceptable carrier substances or vehicles and/or additives or excipients.

Besides the novel compounds of the formula I which are a subject of the present invention as compounds per se, also those compounds comprised by the above definition of the compounds of the formula I which have already been known, upregulate the expression of endothelial NO synthase and are useful medicaments for the treatment of the diseases mentioned above. A subject of the present invention also are those compounds of the formula I which were already known per se, and are not claimed as compounds per se, and their pharmaceutically acceptable salts, for use as transcription stimulating agent or upregulating agent of endothelial NO synthase, for use in the treatment of the diseases mentioned above and in the production of medicaments therefore, and, provided that their use as pharmaceuticals has not yet been known, their use as pharmaceutical, as well as pharmaceutical preparations which comprise an effective dose of at least one of these compounds and/or a pharmaceutically acceptable salt thereof and a pharmaceutically acceptable carrier. Thus, for example, a subject of the present invention are acylamino-substituted heteroaromatic compounds of the formula I,

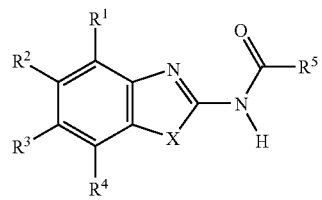

I in any of their stereoisomeric forms and mixtures thereof in any ratio, and the pharmaceutically acceptable salts thereof, wherein in the formula I:

$R^1$ and $R^4$ are independently from each other selected from the group consisting of: H; unsubstituted and at least monosubstituted $C_1$-$C_{10}$-alkyl, $C_2$-$C_{10}$-alkenyl and $C_2$-$C_{10}$-alkynyl, the substituents of which are selected from the group consisting of F, OH, $C_1$-$C_8$-alkoxy, $C_1$-$C_8$-alkylmercapto, —CN, $COOR^6$, $CONR^7R^8$, and unsubstituted and at least monosubstituted phenyl and heteroaryl where the substituents of the phenyl and heteroaryl groups are selected from the group consisting of halogen, —CN, $C_1$-$C_3$-alkyl, $C_1$-$C_3$-alkoxy and $CF_3$; unsubstituted and at least monosubstituted phenyl and heteroaryl the substituents of which are selected from the group consisting of halogen, —CN, $C_1$-$C_3$-alkyl, $C_1$-$C_3$-alkoxy and $CF_3$; $COR^9$; $CONR^{10}R^{11}$; $COOR^{12}$; $CF_3$; halogen; —CN; $NR^{13}R^{14}$; $OR^{15}$; $S(O)_mR^{16}$; $SO_2NR^{17}R^{18}$; and $NO_2$;

$R^2$ and $R^3$ are independently from each other selected from the group consisting of: H; halogen; unsubstituted and at least monosubstituted $C_1$-$C_{10}$-alkyl the substituents of which are selected from the group consisting of OH, phenyl, and heteroaryl; OH; $C_1$-$C_{10}$-alkoxy; phenoxy; $S(O)_mR^{19}$; $CF_3$; —CN; $NO_2$; $C_1$-$C_{10}$-alkylamino; di($C_1$-$C_{10}$-alkyl)amino; ($C_1$-$C_6$-alkyl)-CONH—; unsubstituted and at least monosubstituted phenyl-CONH— and phenyl-$SO_2$—O— the substituents of which are selected from the group consisting of halogen, —CN, methyl and methoxy; $C_1$-$C_6$-alkyl-$SO_2$—O—; unsubstituted and at least monosubstituted ($C_1$-$C_6$-alkyl)-CO— the substituents of which are selected from the group consisting of F, di($C_1$-$C_3$-alkyl)amino, pyrrolidinyl and piperidinyl; and phenyl-CO— the phenyl part of which is unsubstituted or at least monosubstituted by substituents selected from the group consisting of $C_1$-$C_3$-alkyl, halogen and methoxy;

$R^5$ is a group Ar or a group Hetar both of which are unsubstituted or carry one or more identical or different substituents selected from the group consisting of: halogen; —CN; $NH_2$; unsubstituted and at least monosubstituted $C_1$-$C_{10}$-alkyl, $C_2$-$C_{10}$-alkenyl, $C_2$-$C_{10}$-alkynyl, $C_1$-$C_{10}$-alkoxy, $C_1$-$C_{10}$-alkylamino and di($C_1$-$C_{10}$-alkyl)amino, the substituents of which are selected from the group consisting of F, OH, $C_1$-$C_8$-alkoxy, aryloxy, $C_1$-$C_8$-alkylmercapto, $NH_2$, $C_1$-$C_8$-alkylamino and di($C_1$-$C_8$-alkyl)amino; $C_3$-$C_5$-alkandiyl; phenyl; heteroaryl; aryl-substituted or heteroaryl-substituted $C_1$-$C_4$-alkyl; $CF_3$; $NO_2$; OH; phenoxy; benzyloxy; ($C_1$-$C_{10}$-alkyl)-COO—; $S(O)_mR^{20}$; SH; phenylamino; benzylamino; ($C_1$-$C_{10}$-alkyl)-CONH—; ($C_1$-$C_{10}$-alkyl)-CO—N($C_1$-$C_4$-alkyl)-; phenyl-CONH—; phenyl-CO—N($C_1$-$C_4$-alkyl)-; heteroaryl-CONH—; heteroaryl-CO—N($C_1$-$C_4$-alkyl)-; ($C_1$-$C_{10}$-alkyl)-CO—; phenyl-CO—; heteroaryl-CO—; $CF_3$—CO—; —$OCH_2O$—; —$OCF_2O$—; —$OCH_2CH_2O$—; —$CH_2CH_2O$—; $COOR^{21}$; $CONR^{22}R^{23}$; C(NH)—$NH_2$; $SO_2NR^{24}R^{25}$; $R^{26}SO_2NH$—; $R^{27}SO_2N(C_1$-$C_6$-alkyl)-; and a residue of a saturated or at least monounsaturated aliphatic, monocyclic 5-membered to 7-membered heterocycle containing 1, 2 or 3 heteroatoms selected from the group consisting of N, O and S, which heterocycle can be substituted by one or more substituents selected from the group consisting of halogen, $C_1$-$C_3$-alkyl, $C_1$-$C_3$-alkoxy, OH, oxo and $CF_3$, where said heterocycle can optionally be condensed to the said group Ar or the said group Hetar; wherein all aryl, heteroaryl, phenyl, aryl-containing, heteroaryl-containing and phenyl-containing groups, which are optionally present in the said substituents of the said group Ar or the said group Hetar, can be substituted by one or more substituents selected from the group consisting of halogen, —CN, $C_1$-$C_3$-alkyl, OH, $C_1$-$C_3$-alkoxy, and $CF_3$;

$R^6$ is selected from the group consisting of:
H; $C_1$-$C_{10}$-alkyl which can be substituted by one or more substituents selected from the group consisting of F, $C_1$-$C_8$-alkoxy and di($C_1$-$C_8$-alkyl)amino; aryl-($C_1$-$C_4$-alkyl)- and heteroaryl-($C_1$-$C_4$-alkyl)-both of which can be substituted by one or more substituents selected from the group consisting of halogen, $C_1$-$C_4$-alkyl, $C_1$-$C_4$-alkoxy and di($C_1$-$C_6$-alkyl)amino;

$R^7$ is selected from the group consisting of:
H; $C_1$-$C_{10}$-alkyl which can be substituted by one or more substituents selected from the group consisting of F, $C_1$-$C_8$-alkoxy, di($C_1$-$C_8$-alkyl)amino and phenyl; phenyl; indanyl; and heteroaryl; wherein each of the aromatic groups can be unsubstituted or carry one or more substituents selected from the group consisting of halogen, —CN, $C_1$-$C_3$-alkyl, $C_1$-$C_3$-alkoxy and $CF_3$;

$R^8$ is H or $C_1$-$C_{10}$-alkyl;

$R^9$ is selected from the group consisting of:
$C_1$-$C_{10}$-alkyl which can be substituted by one or more substituents from the group consisting of F, $C_1$-$C_4$-alkoxy and di($C_1$-$C_3$-alkyl)amino; and unsubstituted and at least monosubstituted phenyl and heteroaryl the substituents of which are selected from the group consisting of $C_1$-$C_3$-alkyl, $C_1$-$C_3$-alkoxy, halogen, —CN and $CF_3$;

$R^{10}$, independently from $R^7$, is defined as $R^7$;
$R^{11}$, independently from $R^8$, is defined as $R^8$;
$R^{12}$, independently from $R^6$, is defined as $R^6$;
$R^{13}$ is selected from the group consisting of:
H; $C_1$-$C_6$-alkyl; unsubstituted and substituted phenyl, benzyl, heteroaryl, ($C_1$-$C_6$-alkyl)-CO—, phenyl-CO—, and heteroaryl-CO—, the substituents of which are selected from the group consisting of halogen, —CN, $C_1$-$C_3$-alkyl, $C_1$-$C_3$-alkoxy and $CF_3$, wherein one or more of these substituents can be present;

$R^{14}$, independently from $R^{13}$, is defined as $R^{13}$;

$R^{15}$ is selected from the group consisting of:
H; $C_1$-$C_{10}$-alkyl; ($C_1$-$C_3$-alkoxy)-$C_1$-$C_3$-alkyl- and substituted and unsubstituted benzyl, phenyl and heteroaryl, the substituents of which are selected from the group consisting of halogen, —CN, $C_1$-$C_3$-alkyl, $C_1$-$C_3$-alkoxy and $CF_3$, wherein one or more of these substituents can be present;

$R^{16}$ is selected from the group consisting of:
$C_1$-$C_{10}$-alkyl which can be substituted by one or more substituents selected from the group consisting of F, OH, $C_1$-$C_8$-alkoxy, aryloxy, $C_1$-$C_8$-alkylmercapto, $C_1$-$C_8$-alkylamino and di($C_1$-$C_8$-alkyl)amino; $CF_3$; and substituted and unsubstituted phenyl and heteroaryl, the substituents of which are selected from the group consisting of halogen, —CN, $C_1$-$C_3$-alkyl, $C_1$-$C_3$-alkoxy and $CF_3$, wherein one or more of these substitutents can be present;

$R^{17}$, independently from $R^7$, is defined as $R^7$;
$R^{18}$, independently from $R^8$, is defined as $R^8$;
$R^{19}$, independently from $R^{16}$, is defined as $R^{16}$;
$R^{20}$, independently from $R^{16}$, is defined as $R^{16}$;
$R^{21}$, independently from $R^6$, is defined as $R^6$;
$R^{22}$, independently from $R^7$, is defined as $R^7$;
$R^{23}$, independently from $R^8$, is defined as $R^8$;
$R^{24}$, independently from $R^7$, is defined as $R^7$;
$R^{25}$, independently from $R^8$, is defined as $R^8$;
$R^{26}$, independently from $R^{16}$, is defined as $R^{16}$;
$R^{27}$, independently from $R^{16}$, is defined as $R^{16}$;

$R^{30}$ is selected from the group consisting of: H; unsubstituted and at least monosubstituted $C_1$-$C_{10}$-alkyl, $C_2$-$C_{10}$-alkenyl and $C_2$-$C_{10}$-alkynyl, the substituents of which are selected from the group consisting of F, OH, $C_1$-$C_8$-alkoxy, $C_1$-$C_8$-alkylmercapto, —CN, $COOR^{31}$, $CONR^{32}R^{33}$, $NR^{34}R^{35}$, ($C_1$-$C_8$-alkyl)-CONH—, ($C_1$-$C_8$-alkoxy)-CONH—, benzyloxy-CONH— and unsubstituted and at least monosubstituted phenyl and heteroaryl where the substituents of the phenyl and heteroaryl groups are selected from the group consisting of halogen, —CN, $C_1$-$C_3$-alkyl, $C_1$-$C_3$-alkoxy and $CF_3$; and unsubstituted and at least monosubstituted phenyl and heteroaryl the substituents of which are selected from the group consisting of halogen, —CN, $C_1$-$C_3$-alkyl, $C_1$-$C_3$-alkoxy and $CF_3$;

$R^{31}$, independently from $R^6$, is defined as $R^6$;
$R^{32}$, independently from $R^6$, is defined as $R^6$;
$R^{33}$, independently from $R^6$, is defined as $R^6$;
$R^{34}$, independently from $R^6$, is defined as $R^6$;
$R^{35}$, independently from $R^6$, is defined as $R^6$;
X is selected from the group consisting of $NR^{30}$, S, O, CH=CH, N=CH and CH=N;
heteroaryl is a residue of a 5-membered to 10-membered, aromatic, monocyclic or bicyclic heterocycle containing one or more heteroatoms selected from the group consisting of N, O and S;
the group Hetar is a residue of a 5-membered to 10-membered, aromatic, monocyclic or bicyclic heterocycle containing one or more heteroatoms selected from the group consisting of N, O and S;
aryl is phenyl, naphth-1-yl or naphth-2-yl;
the group Ar is phenyl, naphth-1-yl or naphth-2-yl; and
m is 0, 1 or 2;
for use as stimulating agent of the expression of endothelial NO synthase, or for use in the treatment of cardiovascular diseases, stable or unstable angina pectoris, coronary heart disease, Prinzmetal angina, acute coronary syndrome, heart failure, myocardial infarction, stroke, thrombosis, peripheral artery occlusive disease, endothelial dysfunction, atherosclerosis, restenosis, endothel damage after PTCA, hypertension, essential hypertension, pulmonary hypertension, secondary hypertension, renovascular hypertension, chronic glomerulonephritis, erectile dysfunction, ventricular arrhythmia, diabetes, diabetes complications, nephropathy, retinopathy, angiogenesis, asthma bronchiale, chronic renal failure, cirrhosis of the liver, osteoporosis, restricted memory performance or a restricted ability to learn, or for the lowering of cardiovascular risk of postmenopausal women or of women taking contraceptives, and, provided that their use as pharmaceuticals has not yet been known, their use as pharmaceutical as well as pharmaceutical preparations which comprise an effective dose of at least one compound of the formula I and/or a pharmaceutically acceptable salt thereof and a pharmaceutically acceptable carrier. With respect to compounds of the formula I for use as stimulating agent of the expression of endothelial NO synthase or for use as pharmaceutical or for use in the treatment of the beforementioned diseases all explanations given above with respect to the compounds of the formula I per se likewise apply. Thus, a further subject of the invention also are compounds of the formula I for use as stimulating agent of the expression of endothelial NO synthase or for use as pharmaceutical or for use in the treatment of the beforementioned diseases, in which one or more, including all, of the groups and numbers in the definition of the compounds have preferred meanings, more preferred meanings, even more preferred meanings or most preferred meanings or any specific meaning.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously, in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, among others, on the disease to be treated and on its severity.

The amount of a compound of the formula I and/or its pharmaceutically acceptable salts in the pharmaceutical preparations normally ranges from about 0.2 to about 800 mg, preferably from about 0.5 to about 500 mg, in particular from about 1 to about 200 mg, per dose, but depending on the type of the pharmaceutical preparation it may also be higher. The pharmaceutical preparations usually comprise from about 0.5 to about 90% by weight of the compounds of the formula I and/or their pharmaceutically acceptable salts. The production of the pharmaceutical preparations can be carried out in a manner known per se. To this end, one or more compounds of the formula I and/or their pharmaceutically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, or starch derivatives, talc, stearic acid or its salts, etc. Soft gelatin capsules and suppositories can comprise, for example, fats, waxes, semisolid and liquid polyols, natural or hardened oils, etc. Suitable carrier substances for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of the formula I and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the compound or compounds of the invention and carrier substances, the pharmaceutical preparations can also contain additives such as, for example, fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the compound of the formula I to be administered and/or of a pharmaceutically acceptable salt thereof depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the use is for the therapy of a acute or chronic disease or prophylactic, or on whether other active compounds are administered in addition to compounds of the formula I. In general, a daily dose of from about 0.01 to about 100 mg/kg, preferably from about 0.1 to about 10 mg/kg, in particular from about 0.3 to about 5 mg/kg (in each case mg per kg of bodyweight) is appropriate for administration to an adult weighing approximately 75 kg in order to obtain the desired results. The daily dose can be administered in a single dose or, in particular when larger amounts are administered, be divided into several, for example two, three or four individual doses. In some cases, depending on the individual response, it may be necessary to deviate upwards or downwards from the given daily dose.

The compounds of the formula I can also be used for other purposes than those indicated in the foregoing. Non-limiting examples include diagnostic purposes, such as the use in the examination of cell or tissue samples, the use as biochemical tools and the use as intermediates for the preparation of further compounds, e.g. pharmaceutically active compounds.

EXAMPLES

General Procedure for Acylations 66 mg (0.543 mmol) of 4-dimethylaminopyridine, 84 mg (0.543 mmol) of N-(3-dimethylaminopropyl)-N'-ethyl-carbodiimide and 73 mg (0.543 mmol) of 1-hydroxybenzotriazole were added at 0° C. to 0.543 mmol of the respective carboxylic acid dissolved in 2 ml of dry dimethylformamide, and the mixture was stirred for 20 min. 0.543 mmol of the respective heteroaromatic amino compound were then added and the mixture was stirred for 12 h at room temperature. The product isolated by aqueous work-up was purified by preparative HPLC (RP-18; acetonitrile/water+ 0.1% trifluoroacetic acid or formic acid).

In the following listings of example compounds, besides the mass number of the $(M+H)^+$ peak in the mass spectra (MS) obtained from the prepared compound, chromatographic parameters of the prepared compound are given, namely Rf values in the case of characterization by thin layer chromatography (TLC) and retention times (RT; in minutes) in the case of characterization by HPLC. The following chromatographic methods were applied.

Method A (HPLC)

Column: Merck Lichrocart 55-2, Purospher Star, RP 18 e; temperature: 40° C.; flow: 0.750 ml/min; solvent A: acetonitrile/water 90/10+0.5% formic acid; solvent B: acetonitrile/water 10/90+0.5% formic acid; gradient: time 0.00 min: 5% solvent A+95% solvent B, time 0.50 min: 5% solvent A+95% solvent B, time 1.75 min: 95% solvent A+5% solvent B, time 4.25 min: 95% solvent A+5% solvent B, time 4.50 min: 5% solvent A+95% solvent B, time 5.00 min: 5% solvent A+95% solvent B.

Method B (HPLC)

Column: YMC J'Sphere ODS H80, 33×2 mm, 4μ; temperature: 30° C.; flow: 1.000 ml/min; solvent A: acetonitrile+0.05% formic acid; solvent B: water+0.05% formic acid; gradient: time 0.00 min: 10% solvent A+90% solvent B, time 2.50 min: 95% solvent A+5% solvent B, time 3.30 min: 95% solvent A+5% solvent B, time 3.35 min: 10% solvent A+90% solvent B.

Method C(HPLC)

Column: Merck Purospher Star, 55×2 mm, 3μ; temperature: room temperature; flow: 0.45 ml/min; solvent A: acetonitrile+0.1% formic acid; solvent B: water+0.1% formic acid; gradient: time 0.00 min: 5% solvent A+95% solvent B, time 5.00 min: 95% solvent A+5% solvent B, time 7.00 min: 95% solvent A+5% solvent B, time 8.00 min: 5% solvent A+95% solvent B.

Method D (HPLC)

Column: Merck Lichrocart 55-2, Purospher Star, RP 18 e; temperature: 40° C.; flow: 1.000 ml/min; solvent A: acetonitrile/water 90/10+0.5% formic acid; solvent B: acetonitrile/water 10/90+0.5% formic acid; gradient: time 0.00 min: 5% solvent A+95% solvent B, time 0.75 min: 95% solvent A+5% solvent B, time 3.00 min: 95% solvent A+5% solvent B, time 3.20 min: 5% solvent A+95% solvent B, time 4.00 min: 5% solvent A+95% solvent B.

Method E (TLC)

Silica gel; dichloromethane/methanol 98/2.

Method F (TLC)

Silica gel; heptane/ethyl acetate 3/1.

Method G (TLC)

Silica gel; ethyl acetate/heptane 2/1.

Example compounds of the formula Ig are listed in Table 1.

TABLE 1

Example compounds of formula Ig

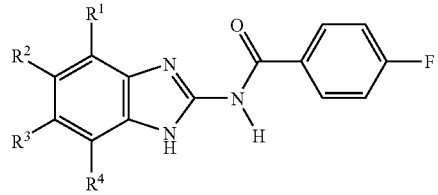

Ig

| Ex. no. | $R^1$ | $R^2$ | $R^3$ | $R^4$ | MS $(M+H)^+$ | HPLC/ TLC | Method |
|---|---|---|---|---|---|---|---|
| 1 | H | H | H | H | 256 | 0.16 | E |
| 2 | H | $nC_3H_7SO_2$ | H | H | 362 | 2.74 | A |
| 3 | H | Cl | Cl | H | 324 | 0.75 | E |
| 4 | H | H | Cl | H | 290 | 0.17 | E |
| 5 | $CH_3$ | H | H | H | 270 | 0.33 | F |
| 6 | H | $CH_3$ | $CH_3$ | H | 284 | | |
| 7 | H | H | $C_6H_5$—S | H | 364 | | |
| 8 | H | H | $C_6H_5$—O | H | 348 | | |
| 9 | $O_2N$ | H | H | H | 301 | 3.041 | A |
| 10 | H | $O_2N$ | H | H | 301 | 2.969 | A |
| 11 | H | HOOC | H | H | 300 | | |
| 12 | H | $C_6H_5$—CO | H | H | 360 | 3.031 | A |
| 13 | H | $CH_3$ | H | H | 270 | 2.749 | A |
| 14 | Br | H | Br | H | 412 | | |
| 15 | H | $CH_3OOC$ | H | H | 324 | 2.912 | A |
| 16 | Cl | H | $CF_3$ | H | 358 | 3.225 | A |
| 17 | H | F | H | H | 274 | 2.885 | A |
| 18 | H | H | $CF_3$ | H | 324 | 3.115 | A |
| 19 | Br | H | $CF_3$ | H | 402 | 3.235 | A |
| 20 | H | F | Cl | H | 308 | 3.057 | A |
| 21 | H | $CH_3O$ | H | H | 286 | 2.692 | A |
| 22 | $CH_3$ | $CH_3$ | H | H | 284 | 2.931 | A |
| 23 | H | $(CH_3)_3C$ | H | H | 312 | 3.035 | A |
| 24 | $CH_3$ | $CH_3$ | Br | H | 362 | 3.231 | A |
| 25 | H | F | F | H | 292 | 2.957 | A |
| 26 | H | $CF_3$ | Cl | H | 358 | 3.166 | A |
| 27 | H | $C_2H_5OOC$ | H | H | 328 | 2.959 | A |
| 28 | H | $CH_3O$ | $CH_3O$ | H | 316 | 2.602 | A |
| 29 | H | $CH_3$ | Cl | H | 304 | 3.030 | A |
| 30 | H | $HO_3S$ | H | H | 336 | 1.175 | A |
| 31 | H | NC | H | H | 281 | 2.893 | A |
| 32 | H | $O_2N$ | F | H | 319 | 2.975 | A |
| 33 | F | H | F | H | 292 | 3.009 | A |
| 34 | $O_2N$ | $CH_3$ | H | H | 315 | 3.106 | A |

$C_6H_5$ denotes phenyl, $nC_3H_7$ denotes n-propyl

Example 35

N-(1-Benzyl-1H-benzimidazol-2-yl)-4-fluorobenzamide

MS: m/e=346 (M+H)$^+$.

Example 36

4-Fluoro-N-(1-phenyl-1H-benzimidazol-2-yl)-benzamide

MS: m/e=332 (M+H)$^+$. HPLC: RT=3.372 min (method A).

Example 37

4-Fluoro-N-(1-isopropyl-5-trifluoromethyl-1H-benzimidazol-2-yl)-benzamide

MS: m/e=366 (M+H)$^+$. HPLC: RT=3.435 min (method A).

Example 38

N-(1-Benzyl-5-trifluoromethyl-1H-benzimidazol-2-yl)-4-fluorobenzamide

MS: m/e=414 (M+H)$^+$. HPLC: RT=3.478 min (method A).

Example 39

N-(1-(2-(3,4-Dimethoxyphenyl)ethyl)-5-trifluoromethyl-1H-benzimidazol-2-yl)-4-fluorobenzamide MS: m/e=488 (M+H)$^+$. HPLC: RT=3.420 min (method A).

Example 40

4-Fluoro-N-(1-(2-(pyridin-2-yl)ethyl)-5-trifluoromethyl-1H-benzimidazol-2-yl)-benzamide MS: m/e=429 (M+H)$^+$. HPLC: RT=3.853 min (method A).

Example 41

4-Fluoro-N-(1-(2-hydroxyethyl)-5-nitro-1H-benzimidazol-2-yl)-benzamide

MS: m/e=345 (M+H)$^+$. HPLC: RT=2.691 min (method A).

Example 42

4-Fluoro-N-(1-(2-phenylethyl)-5-trifluoromethyl-1H-benzimidazol-2-yl)-benzamide

MS: m/e=428 (M+H)$^+$. HPLC: RT=3.534 min (method A).

Example 43

N-(1-Cyanomethyl-1H-benzimidazol-2-yl)-4-fluorobenzamide

MS: m/e=295 (M+H)$^+$. HPLC: RT=2.983 min (method A).

Example 44

4-Fluoro-N-(5-nitro-1-phenyl-1H-benzimidazol-2-yl)-benzamide

MS: m/e=377 (M+H)$^+$. HPLC: RT=3.325 min (method A).

Example 45

N-(5-Chloro-1-ethyl-1H-benzimidazol-2-yl)-4-fluorobenzamide

MS: m/e=318 (M+H)$^+$. HPLC: RT=3.339 min (method A).

Example 46

(2-(2-(4-Fluorobenzoylamino)-5-trifluoromethyl-1H-benzimidazol-1-yl)ethyl)carbamic acid tert-butyl ester MS: m/e=467 (M+H)$^+$. HPLC: RT=3.374 min (method A).

Example 47

4-Fluoro-N-(1-methyl-5-trifluoromethyl-1H-benzimidazol-2-yl)-benzamide

MS: m/e=338 (M+H)$^+$. HPLC: RT=3.111 min (method A).

Example compounds of the formula Ih are listed in Table 2.

TABLE 2

Example compounds of formula Ih

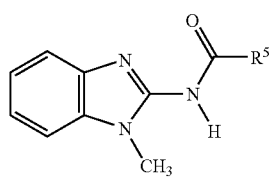

Ih

| Ex. no. | R$^5$ | MS (M + H)$^+$ | HPLC | Method |
|---|---|---|---|---|
| 48 | 4-fluorophenyl | 270 | 4.16 | C |
| 49 | 2,4-dimethyloxazol-5-yl | 271 | 3.57 | C |
| 50 | 3-amino-5-methylpyrazin-2-yl | 283 | 2.66 | C |
| 51 | 2-cyclopropyl-4-methylthiazol-5-yl | 312 | 4.54 | C |
| 52 | 5-amino-1-phenyl-1H-pyrazol-4-yl | 333 | | |
| 53 | 2,6-dimethyl-pyridin-3-yl (a) | 281 | 2.67 | C |
| 54 | 3-amino-5,6-dimethylpyrazin-2-yl (a) | 297 | 2.79 | C |
| 55 | 6-methylaminopyrazin-2-yl | 283 | 2.87 | C |
| 56 | 3-methylsulfonylamino-4-methylphenyl | 359 | 1.94 | B |
| 57 | 2,4-dimethylphenyl | 280 | 3.79 | C |
| 58 | 2,4-difluorophenyl | 288 | 4.37 | C |
| 59 | 5-methylthiophen-2-yl | 272 | 4.61 | C |
| 60 | 4-methylsulfanylphenyl | 298 | 4.68 | C |
| 61 | 5-chlorothiophen-2-yl | 292 | 5.17 | C |
| 62 | 6-dimethylamino-pyridin-3-yl | 296 | 2.81 | C |
| 63 | 3-methylsulfonylaminophenyl | 345 | 3.91 | C |
| 64 | 6-(morpholin-4-yl)pyridin-3-yl (a) | 338 | 3.13 | C |
| 65 | 5,6,7,8-tetrahydroquinolin-3-yl (a) | 307 | 3.03 | C |
| 66 | 6-methoxypyridin-3-yl (a) | 283 | 4.16 | C |
| 67 | 2-methylthiazol-5-yl | 273 | 3.93 | C |

TABLE 2-continued

Example compounds of formula Ih

Ih: [benzimidazole structure with N-CH3 and C(=O)-R5-NH substituent]

| Ex. no. | R⁵ | MS (M+H)⁺ | HPLC | Method |
|---|---|---|---|---|
| 68 | 3-(piperidin-1-yl)phenyl (a) | 335 | 3.21 | C |
| 69 | 3-(4-methylpiperazin-1-yl)phenyl (a) | 350 | 2.83 | C |
| 70 | 3-(morpholin-4-yl)phenyl (a) | 337 | 3.96 | C |
| 71 | 3-(pyridin-4-ylamino)phenyl (a) | 344 | 2.97 | C |
| 72 | 2-methyl-3H-benzimidazol-5-yl (a) | 306 | 2.78 | C |
| 73 | 1-phenyl-5-trifluoromethyl-1H-pyrazol-4-yl | 386 | 5.07 | C |
| 74 | 2,5-dimethyl-1-(pyridin-4-ylmethyl)-1H-pyrrol-3-yl (a) | 360 | 2.43 | C |
| 75 | 2,4-dimethylthiazol-5-yl | 287 | 4.00 | C |
| 76 | 2-aminopyridin-3-yl (a) | 268 | 2.79 | C |
| 77 | 6-methylpyridin-3-yl (a) | 267 | 2.78 | C |
| 78 | 2-chloro-6-methylpyridin-3-yl (a) | 301 | 3.81 | C |
| 79 | 6-methoxymethylpyridin-3-yl (a) | 297 | 3.39 | C |
| 80 | 5-methylpyrazin-2-yl (a) | 268 | 3.16 | |
| 81 | 3-aminopyrazin-2-yl (a) | 269 | 2.58 | C |
| 82 | 1H-indol-6-yl | 291 | 3.67 | C |
| 83 | 1H-indol-5-yl | 291 | 3.42 | C |
| 84 | 1H-indol-4-yl | 291 | 3.35 | C |
| 85 | 3-dimethylaminophenyl (a) | 295 | 3.37 | C |
| 86 | 2,3-dichlorophenyl | 320 | 4.68 | C |

(a) The compound was obtained as salt with trifluoroacetic acid.

Example compounds of the formula Ik are listed in Table 3.

TABLE 3

Example compounds of formula Ik

Ik: [benzothiazole structure with H3C-O and C(=O)-R5-NH substituent]

| Ex. no. | R⁵ | MS (M+H)⁺ | HPLC | Method |
|---|---|---|---|---|
| 87 | 2,3-dichlorophenyl | 353 | 3.15 | A |
| 88 | 2,3-dimethylphenyl | 313 | 1.76 | D |
| 89 | 2,4-dimethylphenyl | 313 | 3.04 | A |
| 90 | 3-dimethylaminophenyl | 328 | 1.89 | D |
| 91 | 3,4-dimethylphenyl | 313 | 3.21 | A |
| 92 | 4-phenoxyphenyl | 377 | 3.32 | A |
| 93 | 4-trifluoromethoxyphenyl | 369 | 1.97 | D |
| 94 | 4-ethylsulfanylphenyl | 345 | 1.95 | D |
| 95 | 6-chloropyridin-3-yl | 320 | 2.03 | D |
| 96 | 2-hydroxy-6-methylpyridin-3-yl | 316 | 1.54 | D |
| 97 | 6-methylpyridin-3-yl | 300 | 1.73 | D |
| 98 | 1H-indol-4-yl | 324 | 1.87 | D |
| 99 | 2,3-difluorophenyl | 321 | 1.95 | D |
| 100 | 1H-benzimidazol-5-yl | 325 | 1.71 | D |
| 101 | 1H-benzotriazol-5-yl | 326 | 2.78 | A |
| 102 | 2-methylpyridin-3-yl (a) | 300 | 2.70 | A |
| 103 | 3-acetylaminophenyl | 342 | 1.82 | D |
| 104 | 4-bromo-2-methylphenyl | 377 | 2.13 | D |
| 105 | 4-trifluoromethylsulfanylphenyl | 385 | 2.19 | D |
| 106 | 4-chloro-2-fluorophenyl | 337 | 2.07 | D |
| 107 | 4-isopropoxyphenyl | 342 | 2.10 | D |
| 108 | 2,4-dimethylthiazol-5-yl | 320 | 1.93 | D |
| 109 | 5-methyl-1-phenyl-1H-pyrazol-4-yl | 365 | 1.96 | D |
| 110 | 5-methylpyrazin-2-yl | 301 | 2.02 | D |
| 111 | 2,6-dimethoxypyridin-3-yl | 346 | 2.27 | D |
| 112 | 2-chloro-6-methylpyridin-3-yl | 334 | 1.98 | D |
| 113 | 4-methyl-2-phenylthiazol-5-yl | 382 | 3.28 | A |
| 114 | 1-phenyl-5-trifluoromethyl-1H-pyrazol-4-yl | 419 | 2.08 | D |
| 115 | 1H-indol-6-yl | 324 | 3.00 | A |
| 116 | 6-trifluoromethylpyridin-3-yl | 354 | 2.01 | D |
| 117 | 2-methyl-1H-benzimidazol-5-yl | 339 | 1.67 | D |
| 118 | 6-cyanopyridin-3-yl | 311 | 1.94 | D |
| 119 | benzo[1,2,3]thiadiazol-5-yl | 343 | 2.98 | A |
| 120 | 5-(thiophen-2-yl)pyridin-3-yl (a) | 368 | 3.15 | A |
| 121 | benz[c]isoxazol-3-yl | 326 | 1.62 | A |

(a) The compound was obtained as salt with formic acid.

Example 122

N-(6-Bromobenzothiazol-2-yl)-4-fluorobenzamide

MS: m/e=351 (M+H)⁺. HPLC: RT=3.26 min (method A).

Example 123

N-(5-Chlorobenzothiazol-2-yl)-4-fluorobenzamide

MS: m/e=307 (M+H)⁺. HPLC: RT=3.15 min (method A).

Example 124

N-(7-Chlorobenzothiazol-2-yl)-4-fluorobenzamide

MS: m/e=307 (M+H)⁺. TLC: Rf=0.45 (method G).

Example 125

N-(5-Chlorobenzoxazol-2-yl)-4-fluorobenzamide

MS: m/e=291 (M+H)⁺. HPLC: RT=2.984 min (method A).

Example 126

4-Fluoro-N-(quinolin-2-yl)-benzamide

MS: m/e=267 (M+H)⁺. TLC: Rf=0.49 (method E).

Determination of Activation of eNOS Transcription

Activation of eNOS transcription was determined as described in detail in Li et al., "Activation of protein kinase C alpha and/or epsilon enhances transcription of the human endothelial nitric oxide synthase gene", Mol. Pharmacol. 53 (1998) 630 (the content of which is incorporated herein by reference). Briefly, a 3.5 kB long fragment 5' of the starting codon of the eNOS gene was cloned, sequenced and cloned in firefly luciferase expression plasmids to monitor activation of the eNOS promoter by reporter gene activity. A human endothelial cell line stable transfected and expressing this promoter-reporter construct was used for compound testing. Cells were incubated for 18 h with compounds.

All compounds were dissolved in sterile dimethyl sulfoxide (DMSO). A final concentration of 0.5% DMSO in complete medium was allowed. Induction of reporter gene expression in these cells was measured using a standard luciferase assay system (Promega, Cat. No E150) according to the manufacturer's instructions. Luciferase induction in cells incubated with compounds were compared to those incubated with solvent alone. The ratio of both activities (transcription induction ratio, TIR) was plotted as a function of compound concentration. Typically, TIR values started at low concentrations at a ratio of 1, indicating no compound effect, and extended up to a maximum TIR value TIR(max) which indicates the increase of the eNOS transcription. $EC_{50}$ values of transcription induction ratios as a function of compound concentration were determined graphically.

The effect of compounds on eNOS-transcription was confirmed in a second assay based on eNOS protein detection. Primary human umbilical vein cord endothelial cells (HUVEC) were isolated and cultivated according to standard procedures. Confluent cells were incubated with compounds for 18 h and the effect on eNOS protein expression determined by a quantitative Western blotting procedure. After compounds incubation, HUVEC were lysed in ice-cold lysis buffer containing 10 mM Tris-HCl, pH 8.0, 1% SDS and protease inhibitors. The lysate was subjected to a standard denaturating polyacrylamide gel electropheresis and blotted to nitrocellulose membranes. Using a specific primary monoclonal antibody (Transaction Laboratories, UK) and alkaline phosphatase labelled secondary antibody (Jackson Labs), a specific eNOS protein band was visualized and quantified based on a chemifluorescence detection method.

The results obtained with example compounds of the invention are listed in Table 4.

TABLE 4

$EC_{50}$ values of transcription induction ratio

| Compound of Example No. | $EC_{50}$ [µM] |
|---|---|
| 1 | 0.028 |
| 4 | <0.1 |
| 5 | 0.35 |
| 6 | 0.31 |
| 9 | 0.050 |
| 13 | 0.065 |
| 17 | <0.1 |
| 20 | <0.1 |
| 21 | 0.29 |
| 22 | 0.086 |
| 23 | 0.048 |
| 25 | <0.1 |
| 29 | 0.084 |
| 33 | 0.079 |
| 34 | 0.18 |
| 48 | 0.21 |
| 90 | 12 |
| 91 | 0.34 |
| 95 | 1.6 |
| 98 | 0.027 |
| 99 | 0.020 |

TABLE 4-continued $EC_{50}$ values of transcription induction ratio

| Compound of Example No. | $EC_{50}$ [µM] |
|---|---|
| 100 | 0.92 |
| 103 | 0.016 |
| 107 | 0.84 |
| 112 | 7.6 |
| 114 | 9.7 |
| 115 | 6.7 |
| 119 | 0.19 |
| 123 | 12 |
| 124 | <0.1 |

The effect of the compounds of the invention can also be investigated in the following animal models (animal experiments are performed in accordance to the German animal protection law and to the guidelines for the use of experimental animals as given by the Guide for the Care and Use of Laboratory Animals of the US National Institutes of Health).

Animals and Treatment (Experiments A-C)

ApoE and eNOS deficient mice (C57BL/6J background, Jackson Laboratory, Bar Harbor, Me) are used. All animals are 10 to 12 weeks of age and weigh 22 to 28 g. Three days before surgery mice are divided into 4 groups (apoE control, n=10 to 12; apoE with test compounds, n=10 to 12; eNOS control, n=10 to 12; eNOS with test compounds, n=10 to 12) and receive either a standard rodent chow (containing 4% fat and 0.001% cholesterol; in the following designated as placebo group) or a standard rodent chow+test compound (10 or 30 mg/kg/d p.o.).

A. Anti-hypertensive Effect in ApoE Knockout Mice

Blood-pressure is determined in conscious mice using a computerized tail-cuff system (Visitech Systems, Apex, Nc). After treatment of ApoE deficient mice and eNOS deficient mice with the test compounds the blood pressure is compared to the results obtained with a placebo treatment.

B. Inhibition of Neointima Formation and Atherogenesis (Femoral Artery Cuff)

After 3 day treatment of ApoE deficient mice with the respective compound, (10 mg/kg/d pressed in chow), animals are anesthetized with an intraperitoneal injection of pentobarbital (60 mg/kg) followed by an intramuscular injection of xylazin (2 mg/kg) and a cuff is placed around the femoral artery as described in Moroi et al.(J. Clin. Invest. 101 (1998) 1225, the content of which is incorporated herein by reference). Briefly, the left femoral artery is dissected. A non-occlusive 2.0 mm polyethylene cuff made of PE-50 tubing (inner diameter 0.56 mm, outer diameter 0.965 mm, Becton Dickinson, Mountain View, Calif.) is placed around the artery and tied in place with two 7-0 sutures. The right femoral artery is isolated from the surrounding tissues but a cuff is not placed. Treatment with the respective compound is continued for 14 days after surgery. Then the animals are sacrificed. The aorta are taken for determination of vascular eNOS expressions by quantitative western blotting. Both femoral arteries are harvested, fixed in formalin and embedded in paraffin. 20 cross sections (10 µm) are cut from the cuffed portion of the left femoral artery and from the corresponding segment of the right artery. Sections are subjected to standard hematoxylin and eosin staining. Morphometric analyses are performed using an image analysis computer program (LeicaQWin, Leica Imaging Systems, Cambridge, GB). For each cross section the area of the lumen, the neointima and the media are determined. To this end, the neointima is defined as the area between the lumen and the internal elastic lamina and the media is defined as the area between the internal and the external elastic lamina. The ratio between the area of the neointima and the area of the media is expressed as the neointima/media ratio. The results obtained in the compound group are compared to those obtained in the placebo group.

C. Prevention of Atherosclerotic Plaque Formation in Chronic Treatment

ApoE deficient mice are treated for 16 weeks with the respective compound pressed in chow and finally sacrificed. Aortas are removed from each mouse, fixed in formalin and embedded in paraffin. Plaque formation is measured via lipid lesions formation in the aortas (from aortic arch to diaphragm) and is analyzed by oil red O staining. For quantifying the effect of the respective compound on vascular eNOS expression the femoral arteries are used in this experiment. The results obtained in the compound group are compared to those obtained in the placebo group.

D. Improvement of Coronary Function in Diseased ApoE Deficient Mice

Old Male wild-type C57BL/6J mice (Charles River Wiga GmbH, Sulzfeld), and apoE deficient mice (C57BL/6J background, Jackson Laboratory, Bar Harbor, Me) 6 month of age and weighing 28 to 36 g are used in the experiments. Mice are divided into 3 groups (C57BL/6, n=8; apoE control, n=8; apoE with respective compound, n=8) and receive for 8 weeks either a standard rodent chow (containing 4% fat and 0.001% cholesterol) or a standard rodent chow+respective compound (30 mg/kg/d p.o.). Mice are anesthetized with sodium pentobarbitone (100 mg/kg i.p.), and the hearts are rapidly excised and placed into ice-cold perfusion buffer. The aorta is cannulated and connected to a perfusion apparatus (Hugo Sachs Electronics, Freiburg, Germany) which is started immediately at a constant perfusion pressure of 60 mm Hg. Hearts are perfused in a retrograde fashion with modified Krebs bicarbonate buffer, equilibrated with 95% $O_2$ and 5% $CO_2$ and maintained at 37.5° C. A beveled small tube (PE 50) is passed through a pulmonary vein into the left ventricle and pulled through the ventricular wall, anchored in the apex by a fluted end, and connected to a tip-micromanometer (Millar 1.4 French). The left atrium is cannulated through the same pulmonary vein and the heart switched to the working mode with a constant preload pressure of 10 mm Hg and an afterload pressure of 60 mm Hg. Aortic outflow and atrial inflow are continuously measured using ultrasonic flow probes (HSE/Transonic Systems Inc.). Coronary flow is calculated as the difference between atrial flow and aortic flow. All hemodynamic data are digitized at a sampling rate of 1000 Hz and recorded with a PC using spezialized software (HEM, Notocord).

Hearts are allowed to stabilize for 30 min. All functional hemodynamic data are measured during steady state, and during volume- and pressure loading. Left ventricular function curves are constructed by varying pre-load pressure. For acquisition of preload curves, afterload is set at 60 mm Hg and preload is adjusted in 5 mm Hg steps over a range of 5 to 25 mm Hg. Hearts are allowed to stabilize at baseline conditions between pressure- and volume-loading.

We claim:
1. A compound of formula I,

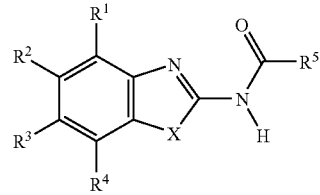

wherein:
$R^1$ and $R^4$ are each, independently,
  H;
  $C_1$-$C_{10}$-alkyl, $C_2$-$C_{10}$-alkenyl or $C_2$-$C_{10}$-alkynyl, each of which is optionally substituted one or more times by F, OH, $C_1$-$C_8$-alkoxy, $C_1$-$C_8$-alkylmercapto, —CN, COOR$^6$, CONR$^7$R$^8$, phenyl or heteroaryl, wherein the phenyl and heteroaryl are each independently optionally substituted one or more times by halogen, —CN, $C_1$-$C_3$-alkyl, $C_1$-$C_3$-alkoxy or CF$_3$;
  phenyl or heteroaryl, each of which is optionally substituted one or more times by halogen, —CN, $C_1$-$C_3$-alkyl, $C_1$-$C_3$-alkoxy or CF$_3$;
  COR$^9$;
  CONR$^{10}$R$^{11}$;
  COOR$^{12}$;
  CF$_3$;
  halogen;
  —CN;
  NR$^{13}$R$^{14}$;
  OR$^{15}$;
  S(O)$_m$R$^{16}$;
  SO$_2$NR$^{17}$R$^{18}$; or
  NO$_2$;
$R^2$ and $R^3$ are each, independently,
  H;
  halogen;
  —CN;
  $C_1$-$C_{10}$-alkyl, optionally substituted one or more times by OH, phenyl, or heteroaryl;
  OH;
  $C_1$-$C_{10}$-alkoxy;
  phenoxy;
  S(O)$_m$R$^{19}$;
  CF$_3$;
  NO$_2$;
  $C_1$-$C_{10}$-alkylamino;
  di($C_1$-$C_{10}$-alkyl)amino;
  ($C_1$-$C_6$-alkyl)-CONH—;
  phenyl-CONH— or phenyl-SO$_2$—O—, wherein the phenyl is optionally substituted one or more times by halogen, —CN, methyl or methoxy;
  $C_1$-$C_6$-alkyl-SO$_2$—O—;
  ($C_1$-$C_6$-alkyl)-CO—, wherein the $C_1$-$C_6$-alkyl is optionally substituted one or more times by F, di($C_1$-$C_3$-alkyl)amino, pyrrolidinyl or piperidinyl; or
  phenyl-CO—, wherein the phenyl is optionally substituted one or more times by $C_1$-$C_3$-alkyl, halogen or methoxy;
$R^5$ is indolyl which is optionally substituted one or more times by
  halogen;
  —CN;
  NH$_2$;
  $C_1$-$C_{10}$-alkyl, $C_2$-$C_{10}$-alkenyl, $C_2$-$C_{10}$-alkynyl, $C_1$-$C_{10}$-alkoxy, $C_1$-$C_{10}$-alkylamino or di($C_1$-$C_{10}$-alkyl)

amino, wherein the alkyl, alkenyl, alkynyl and alkoxy are each independently optionally substituted one or more times by F, OH, $C_1$-$C_8$-alkoxy, aryloxy, $C_1$-$C_8$-alkylmercapto, $NH_2$, $C_1$-$C_8$-alkylamino or di($C_1$-$C_8$-alkyl)amino;

$C_3$-$C_5$-alkandiyl;

phenyl;

heteroaryl;

aryl-substituted or heteroaryl-substituted $C_1$-$C_4$-alkyl;

$NO_2$;

OH;

phenoxy;

benzyloxy;

($C_1$-$C_{10}$-alkyl)-COO—;

$S(O)_m R^{20}$;

SH;

phenylamino;

benzylamino;

($C_1$-$C_{10}$-alkyl)-CONH—;

($C_1 C_{10}$-alkyl)-CO—N($C_1$-$C_4$-alkyl)-;

phenyl-CONH—;

phenyl-CO—N($C_1$-$C_4$-alkyl)-;

heteroaryl-CONH—;

heteroaryl-CO—N($C_1$-$C_4$-alkyl)-;

($C_1$-$C_{10}$-alkyl)-CO—;

phenyl-CO—;

heteroaryl-CO—;

$CF_3$—CO—;

—$OCH_2O$—;

—$OCF_2O$—;

—$OCH_2CH_2O$—;

—$CH_2CH_2O$—;

$COOR^{21}$;

$CONR^{22}R^{23}$;

$C(NH)$—$NH_2$;

$SO_2NR^{24}R^{25}$;

$R^{26}SO_2NH$—;

$R^{27}SO_2N(C_1$-$C_6$-alkyl)-; or a residue of a saturated or unsaturated aliphatic, monocyclic 5-membered to 7-membered heterocycle containing 1, 2 or 3 heteroatoms selected from the group consisting of N, O and S, wherein the heterocycle is optionally substituted one or more times by halogen, $C_1$-$C_3$-alkyl, $C_1$-$C_3$-alkoxy, OH, oxo or $CF_3$, and the heterocycle is optionally condensed to the indolyl group;

provided that $R^5$ is not substituted by $CF_3$; and wherein all aryl, heteroaryl, phenyl, aryl-containing, heteroaryl-containing and phenyl-containing groups, which are optionally present in the said substituents of the indolyl group, can be substituted by one or more substituents selected from the group consisting of halogens, —CN, $C_1$-$C_3$-alkyl, OH, $C_1$-$C_3$-alkoxy, and $CF_3$;

$R^6$ is H;

$C_1$-$C_{10}$-alkyl, optionally substituted one or more times by F, $C_1$-$C_8$-alkoxy or di($C_1$-$C_8$-alkyl)amino;

aryl-($C_1$-$C_4$-alkyl)- or heteroaryl-($C_1$-$C_4$-alkyl)-either of which is optionally substituted one or more times by halogen, $C_1$-$C_4$-alkyl, $C_1$-$C_4$-alkoxy or di($C_1$-$C_6$-alkyl)amino;

$R^7$ is H;

$C_1$-$C_{10}$-alkyl, optionally substituted one or more times by F, $C_1$-$C_8$-alkoxy, di($C_1$-$C_8$-alkyl)amino or phenyl; or phenyl, indanyl or heteroaryl, each of which is optionally substituted one or more times by halogen, —CN, $C_1$-$C_3$-alkyl, $C_1$-$C_3$-alkoxy or $CF_3$;

$R^8$ is H or $C_1$-$C_{10}$-alkyl;

$R^9$ is $C_1$-$C_{10}$-alkyl, optionally substituted one or more times by F, $C_1$-$C_4$-alkoxy or di($C_1$-$C_3$-alkyl)amino; or phenyl or heteroaryl, each of which is optionally substituted one or more times by $C_1$-$C_3$-alkyl, $C_1$-$C_3$-alkoxy, halogen, —CN or $CF_3$;

$R^{10}$, independently from $R^7$, is $R^7$;

$R^{11}$, independently from $R^8$, is $R^8$;

$R^{12}$, independently from $R^6$, is $R^6$;

$R^{13}$ is H;

$C_1$-$C_6$-alkyl; or phenyl, benzyl, heteroaryl, ($C_1$-$C_6$-alkyl)-CO—, phenyl-CO—, or heteroaryl-CO—, each of which is optionally substituted one or more times by halogen, —CN, $C_1$-$C_3$-alkyl, $C_1$-$C_3$-alkoxy or $CF_3$;

$R^{14}$, independently from $R^{13}$, is $R^{13}$;

$R^{15}$ is H;

$C_1$-$C_{10}$-alkyl;

($C_1$-$C_3$-alkoxy)-$C_1$-$C_3$-alkyl-;

benzyl, phenyl or heteroaryl, each of which is optionally substituted one or more times by halogen, —CN, $C_1$-$C_3$-alkyl, $C_1$-$C_3$-alkoxy or $CF_3$;

$R^{16}$ is $C_1$-$C_{10}$-alkyl, optionally substituted one or more times by F, OH, $C_1$-$C_8$-alkoxy, aryloxy, $C_1$-$C_8$-alkylmercapto, $C_1$-$C_8$-alkylamino or di($C_1$-$C_8$-alkyl)amino;

$CF_3$; or phenyl or heteroaryl, each of which is optionally substituted one or more times by halogen, —CN, $C_1$-$C_3$-alkyl, $C_1$-$C_3$-alkoxy or $CF_3$;

$R^{17}$, independently from $R^7$, is $R^7$;

$R^{18}$, independently from $R^8$, is $R^8$;

$R^{19}$, independently from $R^{16}$, is $R^{16}$;

$R^{20}$, independently from $R^{16}$, is $R^{16}$;

$R^{21}$, independently from $R^6$, is $R^6$;

$R^{22}$, independently from $R^7$, is $R^7$;

$R^{23}$, independently from $R^8$, is $R^8$;

$R^{24}$, independently from $R^7$, is $R^7$;

$R^{25}$, independently from $R^8$, is $R^8$;

$R^{26}$, independently from $R^{16}$, is $R^{16}$;

$R^{27}$, independently from $R^{16}$, is $R^{16}$;

$R^{30}$ is H;

$C_1$-$C_{10}$-alkyl, $C_2$-$C_{10}$-alkenyl or $C_2$-$C_{10}$-alkynyl, each of which is optionally substituted one or more times by F, OH, $C_1$-$C_8$-alkoxy, $C_1$-$C_8$-alkylmercapto, CN, $COOR^{31}$, $CONR^{32}R^{33}$, $NR^{34}R^{35}$, ($C_1$-$C_8$-alkyl)-CONH—, ($C_1$-$C_8$-alkoxy)-CONH—, benzyloxy-CONH—, phenyl or heteroaryl, wherein the phenyl and heteroaryl are each independently optionally substituted one or more times by halogen, —CN, $C_1$-$C_3$-alkyl, $C_1$-$C_3$-alkoxy or $CF_3$; or phenyl or heteroaryl, each of which is optionally substituted one or more times by halogen, —CN, $C_1$-$C_3$-alkyl, $C_1$-$C_3$-alkoxy or $CF_3$;

$R^{31}$, independently from $R^6$, is $R^6$;

$R^{32}$, independently from $R^6$, is $R^6$;

$R^{33}$, independently from $R^6$, is $R^6$;

$R^{34}$, independently from $R^6$, is $R^6$;

$R^{35}$, independently from $R^6$, is $R^6$;

X is S;

heteroaryl is a residue of a 5-membered to 10-membered, aromatic, monocyclic or bicyclic heterocycle containing one or more heteroatoms selected from the group consisting of N, O and S;

aryl is phenyl, naphth-1-yl or naphth-2-yl; and m is 0, 1 or 2;

or a stereoisomer or a mixture of stereoisomers thereof in any ratio, or a pharmaceutically acceptable salt thereof.

2. The compound according to claim 1, wherein:

$R^1$ and $R^4$ are each, independently,

H;

Halogen; or $C_1$-$C_4$-alkyl;

and

R² and R³ are each, independently,
H;
Halogen; or
$C_1$-$C_4$-alkyl.

3. The compound according to claim 1, wherein:
R⁵ is indolyl which is optionally substituted one or more times by
halogen;
—CN;
$NH_2$;
$C_1$-$C_6$-alkyl, $C_2$-$C_6$-alkenyl, $C_2$-$C_6$-alkynyl, $C_1$-$C_3$-alkoxy, $C_1$-$C_4$-alkyl)amino, each of which is optionally substituted one or more times by F, $C_1$-$C_3$-alkoxy, $C_1$-$C_3$-alkylmercapto or $NH_2$;
$C_3$-$C_5$-alkandiyl;
phenyl;
heteroaryl;
phenyl-substituted or heteroaryl-substituted $C_1$-$C_2$-alkyl;
OH;
($C_1$-$C_4$-alkyl)-COO;
$S(O)_m$—($C_1$-$C_4$)-alkyl;
($C_1$-$C_4$-alkyl)-CONH—;
($C_1$-$C_4$-alkyl)-CON($C_1$-$C_4$-alkyl)-;
($C_1$-$C_4$-alkyl)-CO—;
phenyl-CO—;
heteroaryl-CO—;
$CF_3$—CO—;
—$OCH_2O$—;
—$OCF_2O$—;
—$OCH_2CH_2O$—;
—$CH_2CH_2O$—;
—COO($C_1$-$C_6$-alkyl);
—$CONH_2$;
—CONH($C_1$-$C_4$-alkyl);
—CON(di($C_1$-$C_4$-alkyl));
—C(NH)$NH_2$;
—$SO_2NH_2$;
—$SO_2$NH($C_1$-$C_4$-alkyl);
—$SO_2$NH(phenyl);
—$SO_2$N(di($C_1$-$C_4$-alkyl));
($C_1$-$C_4$-alkyl)-$SO_2$NH—;
($C_1$-$C_4$-alkyl)-$SO_2$N($C_1$-$C_4$-alkyl)-; or
a residue of a saturated or unsaturated aliphatic, mononuclear 5-membered to 7-membered heterocycle containing 1, 2 or 3 heteroatoms selected from the group consisting of N, O and S, wherein the heterocycle is optionally substituted one or more times by halogen, $C_1$-$C_3$-alkyl, $C_1$-$C_3$-alkoxy, OH, oxo or $CF_3$, and the heterocycle is optionally condensed to the indolyl group;
provided that R⁵ is not substituted by $CF_3$; and
wherein all heteroaryl, phenyl, heteroaryl-containing and phenyl-containing groups, which are optionally present in the said substituents of the indolyl group, can be substituted by one or more substituents selected from the group consisting of halogen, —CN, $C_1$-$C_3$-alkyl, OH, $C_1$-$C_3$-alkoxy, and $CF_3$.

4. A pharmaceutical composition comprising a pharmaceutically effective amount of the compound according to claim 1 and a pharmaceutically acceptable carrier.

5. The compound according to claim 1, wherein
R⁵ is indolyl which is attached via ring carbon atom and which is optionally substituted one or more times by:
halogen;
—CN;
$NH_2$;
$C_1$-$C_{10}$-alkyl, $C_2$-$C_{10}$-alkenyl, $C_2$-$C_{10}$-alkynyl, $C_1$-$C_{10}$-alkoxy, $C_1$-$C_{10}$-alkylamino or di($C_1$-$C_{10}$-alkyl)amino, wherein the alkyl, alkenyl, alkynyl and alkoxy are each independently optionally substituted one or more times by F, OH, $C_1$-$C_8$-alkoxy, aryloxy, $C_1$-$C_8$-alkylmercapto, $NH_2$, $C_1$-$C_8$-alkylamino or di($C_1$-$C_8$-alkyl)amino;
$C_3$-$C_5$-alkandiyl;
phenyl;
heteroaryl;
aryl-substituted or heteroaryl-substituted $C_1$-$C_4$-alkyl;
$NO_2$;
OH;
phenoxy;
benzyloxy;
($C_1$-$C_{10}$-alkyl)-COO—;
$S(O)_mR^{20}$;
SH;
phenylamino;
benzylamino;
($C_1$-$C_{10}$-alkyl)-CONH—;
($c_1$-$C_{10}$-alkyl)-CO—N($C_1$-$C_4$-alkyl)-;
phenyl-CONH—;
phenyl-CO—N($C_1$-$C_4$-alkyl)-;
heteroaryl-CONH—;
heteroaryl-CO—N($C_1$-$C_4$-alkyl)-;
($C_1$-$C_{10}$-alkyl)-CO—;
phenyl-CO—;
heteroaryl-CO—;
$CF_3$—CO—;
—$OCH_2O$—;
—$OCF_2O$—;
—$OCH_2CH_2O$—;
—$CH_2CH_2O$—;
$COOR^{21}$;
$CONR^{22}R^{23}$;
C(NH)—$NH_2$;
$SO_2NR^{24}R^{25}$;
$R^{26}SO_2NH$—;
$R^{27}SO_2N(C_1$-$C_6$-alkyl)-; or
a residue of a saturated or unsaturated aliphatic, monocyclic 5-membered to 7-membered heterocycle containing 1, 2 or 3 heteroatoms selected from the group consisting of N, O and S, wherein the heterocycle is optionally substituted one or more times by halogen, $C_1$-$C_3$-alkyl, $C_1$-$C_3$-alkoxy, OH, oxo or $CF_3$, and the heterocycle is optionally condensed to the indolyl group;
provided that R⁵ is not substituted by $CF_3$; and
wherein all aryl, heteroaryl, phenyl, aryl-containing, heteroaryl-containing and phenyl-containing groups, which are optionally present in the said substituents of the indolyl group, can be substituted by one or more substituents selected from the group consisting of halogens, —CN, $C_1$-$C_3$-alkyl, OH, $C_1$-$C_3$-alkoxy, and $CF_3$.

6. The compound according to claim 1 of formula Ik:

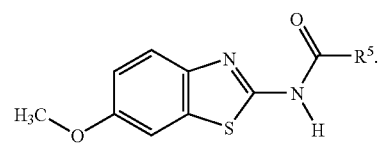

Ik

* * * * *